United States Patent
Williams et al.

(10) Patent No.: US 8,435,295 B2
(45) Date of Patent: May 7, 2013

(54) SYSTEM AND METHOD FOR INTERVERTEBRAL IMPLANT DELIVERY AND REMOVAL

(75) Inventors: Lytton A. Williams, Los Angeles, CA (US); Daniel F. Justin, Logan, UT (US); Darin R. Ewer, Providence, UT (US); Raymond Joseph Gardocki, Germantown, TN (US)

(73) Assignee: Infinity Orthopaedics Company, Newport, CA (US)

( * ) Notice: Subject to any disclaimer, the term of this patent is extended or adjusted under 35 U.S.C. 154(b) by 1607 days.

(21) Appl. No.: 11/535,033

(22) Filed: Sep. 25, 2006

(65) Prior Publication Data

US 2007/0073311 A1    Mar. 29, 2007

Related U.S. Application Data

(60) Provisional application No. 60/720,513, filed on Sep. 26, 2005, provisional application No. 60/720,514, filed on Sep. 26, 2005, provisional application No. 60/741,513, filed on Nov. 30, 2005.

(51) Int. Cl.
*A61B 17/58* (2006.01)
*A61B 17/88* (2006.01)
*A61F 2/28* (2006.01)

(52) U.S. Cl.
USPC ............................ 623/17.11; 606/279; 606/99

(58) Field of Classification Search ............... 606/87, 606/88, 90, 99, 96, 245, 279, 640, 86 A; 600/228–231
See application file for complete search history.

(56) References Cited

U.S. PATENT DOCUMENTS

| | | | |
|---|---|---|---|
| 3,875,595 | A | 4/1975 | Froning |
| 4,309,777 | A | 1/1982 | Patil |
| 4,349,921 | A | 9/1982 | Kuntz |
| 4,401,112 | A | 8/1983 | Rezaian |
| 4,501,269 | A | 2/1985 | Bagby |
| 4,553,273 | A | 11/1985 | Wu |
| 4,554,914 | A | 11/1985 | Kapp |
| 4,599,086 | A | 7/1986 | Doty |
| 4,627,853 | A | 12/1986 | Campbell |
| 4,636,217 | A | 1/1987 | Ogilvie |

(Continued)

FOREIGN PATENT DOCUMENTS

| | | |
|---|---|---|
| EP | 188954 A1 | 7/1986 |
| EP | 538183 A1 | 4/1993 |

(Continued)

OTHER PUBLICATIONS

ProDisc, *Spine Solutions*; Product Brochure p. 1-10.

*Primary Examiner* — Kevin T Truong
*Assistant Examiner* — Matthew Lawson
(74) *Attorney, Agent, or Firm* — G. Jo Hays; James Larson; Barbara Daniels

(57) ABSTRACT

An implant system provides motion preservation or stabilization between two spinal vertebrae. An associated instrumentation system is capable of delivering and removing the implants from either the anterior, left lateral or right lateral positions. The instrumentation system also provides instrumentation for delivering the implant end plates into the disc space, adjusting the position of the end plates in situ, compressing end plates into the vertebral bodies, interoperatively determining the height and angulation of bearings, delivering bearings together and then independently connecting them to the end plates. The system provides alternative instrumentation for revising the motion preservation disc from at least three directions. The system further provides alternative instrumentation for converting the motion preservation disc system to an interbody fusion device from at least three directions.

27 Claims, 33 Drawing Sheets

U.S. PATENT DOCUMENTS

| | | | |
|---|---|---|---|
| 4,678,470 A | 7/1987 | Nashef | |
| 4,714,469 A | 12/1987 | Kenna | |
| 4,743,256 A | 5/1988 | Brantigan | |
| 4,743,259 A | 5/1988 | Bolander | |
| 4,759,766 A | 7/1988 | Buettner-Janz et al. | |
| 4,759,769 A | 7/1988 | Hedman | |
| 4,834,757 A | 5/1989 | Brantigan | |
| 4,863,476 A | 9/1989 | Shepperd | |
| 4,878,915 A | 11/1989 | Brantigan | |
| 4,892,545 A | 1/1990 | Day | |
| 4,932,975 A | 6/1990 | Main | |
| 4,961,740 A | 10/1990 | Ray | |
| 4,971,037 A * | 11/1990 | Pelta | 600/234 |
| 4,997,432 A | 3/1991 | Keller | |
| 5,015,247 A | 5/1991 | Michelson | |
| 5,026,373 A | 6/1991 | Ray | |
| 5,055,104 A | 10/1991 | Ray | |
| 5,059,193 A | 10/1991 | Kuslich | |
| 5,062,850 A | 11/1991 | MacMillan | |
| 5,071,437 A | 12/1991 | Steffee | |
| 5,123,926 A | 6/1992 | Pisharodi | |
| 5,147,402 A | 9/1992 | Bohler | |
| 5,192,327 A | 3/1993 | Brantigan | |
| 5,236,460 A | 8/1993 | Barber | |
| 5,258,031 A | 11/1993 | Salib | |
| 5,263,953 A | 11/1993 | Bagby | |
| 5,290,312 A | 3/1994 | Kojimoto | |
| 5,306,310 A | 4/1994 | Siebels | |
| 5,314,477 A * | 5/1994 | Marnay | 623/17.15 |
| 5,336,223 A | 8/1994 | Rogers | |
| 5,370,697 A | 12/1994 | Baumgartner | |
| 5,397,364 A | 3/1995 | Kozak | |
| 5,401,269 A | 3/1995 | Buttner-Janz | |
| 5,417,975 A | 5/1995 | Lussi | |
| 5,425,769 A | 6/1995 | Snyders, Jr. | |
| 5,425,773 A | 6/1995 | Boyd | |
| 5,439,684 A | 8/1995 | Prewett | |
| 5,455,231 A | 10/1995 | Constantz | |
| 5,458,641 A | 10/1995 | Ramirez Jimenez | |
| 5,464,439 A | 11/1995 | Gendler | |
| 5,480,442 A | 1/1996 | Bertagnoli | |
| 5,507,813 A | 4/1996 | Dowd | |
| 5,507,816 A | 4/1996 | Bullivant | |
| 5,510,396 A | 4/1996 | Prewett | |
| 5,522,899 A | 6/1996 | Michelson | |
| 5,534,030 A | 7/1996 | Navarro | |
| 5,549,679 A | 8/1996 | Kuslich | |
| 5,554,191 A | 9/1996 | Lahille | |
| 5,556,431 A | 9/1996 | Buttner-Janz | |
| 5,562,738 A | 10/1996 | Boyd et al. | |
| 5,585,116 A | 12/1996 | Boniface | |
| 5,609,635 A | 3/1997 | Michelson | |
| 5,645,591 A | 7/1997 | Kuberasampath | |
| 5,653,763 A | 8/1997 | Errico | |
| 5,658,335 A | 8/1997 | Allen | |
| 5,665,122 A | 9/1997 | Kambin | |
| 5,676,701 A | 10/1997 | Yuan | |
| 5,683,465 A | 11/1997 | Shinn | |
| 5,693,100 A | 12/1997 | Pisharodi | |
| 5,702,391 A | 12/1997 | Lin | |
| 5,702,450 A | 12/1997 | Bisserie | |
| 5,702,453 A | 12/1997 | Rabbe | |
| 5,702,455 A | 12/1997 | Saggar | |
| 5,713,904 A | 2/1998 | Errico | |
| 5,720,751 A * | 2/1998 | Jackson | 606/86 R |
| 5,749,916 A | 5/1998 | Richelsoph | |
| 5,776,197 A | 7/1998 | Rabbe | |
| 5,776,199 A | 7/1998 | Michelson | |
| 5,782,832 A | 7/1998 | Larsen | |
| 5,800,550 A | 9/1998 | Sertich | |
| 5,888,227 A | 3/1999 | Cottle | |
| 5,895,428 A | 4/1999 | Berry | |
| 5,899,941 A | 5/1999 | Nishijima | |
| 5,916,267 A | 6/1999 | Tienboon | |
| 5,980,522 A | 11/1999 | Koros et al. | |
| 5,989,290 A | 11/1999 | Biedermann | |
| 6,015,436 A | 1/2000 | Schonhoffer | |
| 6,019,792 A | 2/2000 | Cauthen | |
| 6,039,763 A | 3/2000 | Shelokov | |
| 6,045,579 A | 4/2000 | Hochshuler | |
| 6,080,193 A | 6/2000 | Hochshuler | |
| 6,090,114 A * | 7/2000 | Matsuno et al. | 606/88 |
| 6,102,950 A | 8/2000 | Vaccaro | |
| 6,106,557 A | 8/2000 | Robioneck | |
| 6,113,637 A | 9/2000 | Gill et al. | |
| 6,113,638 A | 9/2000 | Williams | |
| 6,146,421 A | 11/2000 | Gordon et al. | |
| 6,176,881 B1 | 1/2001 | Schar | |
| 6,176,882 B1 | 1/2001 | Biedermann et al. | |
| 6,179,874 B1 | 1/2001 | Cauthen | |
| 6,217,579 B1 | 4/2001 | Koros | |
| 6,228,118 B1 | 5/2001 | Gordon | |
| 6,344,057 B1 | 2/2002 | Rabbe | |
| 6,375,681 B1 | 4/2002 | Truscott | |
| 6,375,683 B1 | 4/2002 | Crozet | |
| 6,402,785 B1 | 6/2002 | Zdeblick | |
| 6,419,704 B1 | 7/2002 | Ferree | |
| 6,440,168 B1 | 8/2002 | Cauthen | |
| 6,517,580 B1 | 2/2003 | Ramadan et al. | |
| 6,524,641 B1 | 2/2003 | de Witzmann | |
| 6,540,785 B1 | 4/2003 | Gill et al. | |
| 6,576,016 B1 | 6/2003 | Hochshuler et al. | |
| 6,641,614 B1 | 11/2003 | Wagner et al. | |
| 6,663,616 B1 * | 12/2003 | Roth et al. | 606/1 |
| 6,679,915 B1 | 1/2004 | Cauthen | |
| 6,706,070 B1 | 3/2004 | Wagner et al. | |
| 6,726,720 B2 | 4/2004 | Ross et al. | |
| 6,800,092 B1 | 10/2004 | Williams et al. | |
| 6,860,877 B1 * | 3/2005 | Sanchez et al. | 606/1 |
| 6,899,735 B2 | 5/2005 | Coates et al. | |
| 7,118,580 B1 * | 10/2006 | Beyersdorff et al. | 606/99 |
| 7,169,153 B2 * | 1/2007 | Keller | 606/99 |
| 7,276,082 B2 * | 10/2007 | Zdeblick et al. | 623/17.15 |
| 2002/0116009 A1 * | 8/2002 | Fraser et al. | 606/99 |
| 2002/0161441 A1 | 10/2002 | Lang | |
| 2003/0032962 A1 * | 2/2003 | McGahan et al. | 606/80 |
| 2003/0135220 A1 * | 7/2003 | Cauthen | 606/87 |
| 2003/0135277 A1 * | 7/2003 | Bryan et al. | 623/17.12 |
| 2003/0187454 A1 | 10/2003 | Gill et al. | |
| 2003/0208272 A1 | 11/2003 | Crozet | |
| 2003/0229355 A1 * | 12/2003 | Keller | 606/99 |
| 2004/0002758 A1 * | 1/2004 | Landry et al. | 623/17.11 |
| 2004/0010316 A1 | 1/2004 | Williams et al. | |
| 2004/0102790 A1 * | 5/2004 | Ralph et al. | 606/99 |
| 2004/0167537 A1 * | 8/2004 | Errico et al. | 606/99 |
| 2004/0220582 A1 * | 11/2004 | Keller | 606/99 |
| 2004/0225295 A1 * | 11/2004 | Zubok et al. | 606/90 |
| 2004/0236342 A1 * | 11/2004 | Ferree et al. | 606/102 |
| 2004/0243240 A1 * | 12/2004 | Beaurain et al. | 623/17.14 |
| 2004/0260396 A1 | 12/2004 | Ferree et al. | |
| 2005/0021042 A1 * | 1/2005 | Marnay et al. | 606/99 |
| 2005/0027362 A1 | 2/2005 | Williams et al. | |
| 2005/0055095 A1 * | 3/2005 | Errico et al. | 623/17.11 |
| 2005/0060034 A1 | 3/2005 | Berry et al. | |
| 2005/0119665 A1 * | 6/2005 | Keller | 606/99 |
| 2005/0268400 A1 * | 12/2005 | Siccardi et al. | 5/621 |
| 2006/0064107 A1 * | 3/2006 | Bertagnoli et al. | 606/99 |
| 2006/0116768 A1 * | 6/2006 | Krueger et al. | 623/17.14 |
| 2007/0016221 A1 * | 1/2007 | Beyersdorff et al. | 606/99 |
| 2007/0100346 A1 * | 5/2007 | Wyss et al. | 606/87 |
| 2007/0156243 A1 * | 7/2007 | Errico et al. | 623/17.14 |
| 2007/0233152 A1 * | 10/2007 | Stad et al. | 606/99 |
| 2008/0183178 A1 * | 7/2008 | Collazo | 606/88 |

FOREIGN PATENT DOCUMENTS

| | | |
|---|---|---|
| EP | 610837 A1 | 8/1994 |
| EP | 425542 B1 | 3/1995 |
| EP | 1161205 A1 | 8/2000 |
| WO | WO9214423 A1 | 9/1992 |
| WO | WO9310725 A2 | 6/1993 |
| WO | WO9404100 A1 | 3/1994 |
| WO | WO9700054 A1 | 1/1997 |
| WO | WO0049977 C2 | 8/2000 |
| WO | WO0217825 A2 | 3/2002 |

* cited by examiner

SYSTEM AND METHOD FOR INTERVERTEBRAL IMPLANT DELIVERY AND REMOVAL

CROSS-REFERENCE TO RELATED APPLICATIONS

This application claims the benefit of the following:

U.S. Provisional Application No. 60/720,513, filed Sep. 26, 2005, which carries and is entitled MODULAR ARTICULATING AND FUSION SPINAL DISC IMPLANT SYSTEM;

U.S. Provisional Application No. 60/720,514, filed Sep. 26, 2005, which carries and is entitled UNIVERSAL SPINAL DISC IMPLANT SYSTEM FOR PROVIDING INTERVERTEBRAL ARTICULATION AND FUSION; and U.S. Provisional Application No. 60/741,513, filed Nov. 30, 2005, which carries and is entitled SYSTEM AND METHOD FOR INTERVERTEBRAL IMPLANT DELIVERY AND REMOVAL.

All of the foregoing are incorporated herein by reference.

BACKGROUND OF THE INVENTION

1. The Field of the Invention

The present invention relates generally to spinal orthopedics, and more precisely, to intervertebral implants and related instrumentation.

2. The Relevant Technology

Severe back pain can be caused by sa number of different ailments, including spinal stenosis, degenerative disc disease, spondylolisthesis, and the like. Many such ailments can be corrected by controlling or limiting relative motion between the affected vertebrae. Accordingly, a variety of devices including artificial discs and fusion devices have been proposed.

A variety of instruments have also been proposed for use with such intervertebral devices. These instruments are typically limited to use with one implant configuration and/or one surgical approach. Accordingly, many known instruments are usable only when the indications fit within a relatively narrow set of criteria. Furthermore, the soft tissue damage often caused by operation in the intervertebral disc space may prevent any revision surgery from being carried out along the same approach. Thus, many known instruments are not usable for revision of an existing intervertebral treatment.

Further, many known instruments are expensive or difficult to manufacture, or are difficult to use. Accordingly, there is a need in the art for instrumentation that remedies these problems.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
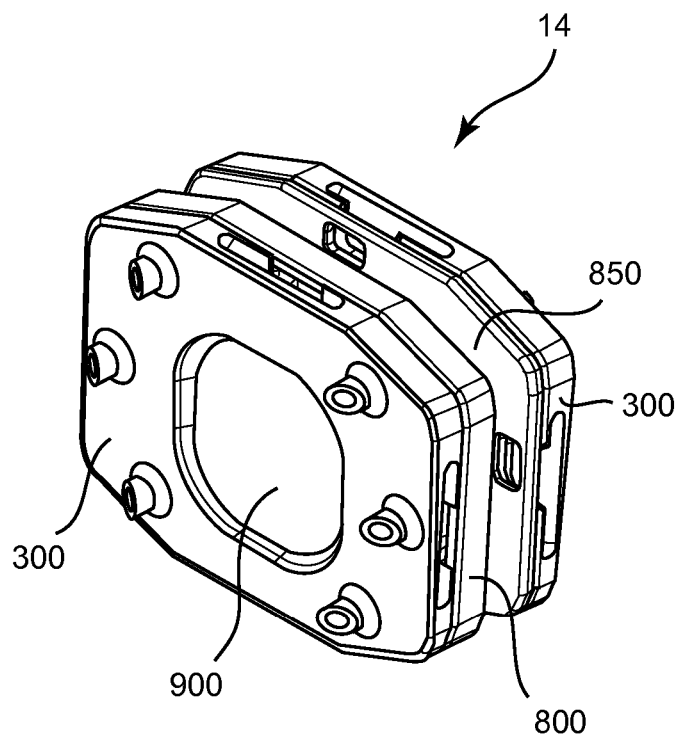
FIG. 1 is a perspective view of an intervertebral disc motion preservation implant in an assembled state.

FIG. 1 illustrates an intervertebral disc motion preservation implant 14. The implant 14 is designed for placement between spinal vertebrae to replace degenerated intervertebral disc material. The implant 14 comprises two end plates 300, a superior bearing 800, and an inferior bearing 850, and two snap fasteners 900. The end plates 300 are implanted in the vertebral bodies, and the snap fasteners 900 hold the bearings 800, 850 in place between the end plates 300.

Figure 2:
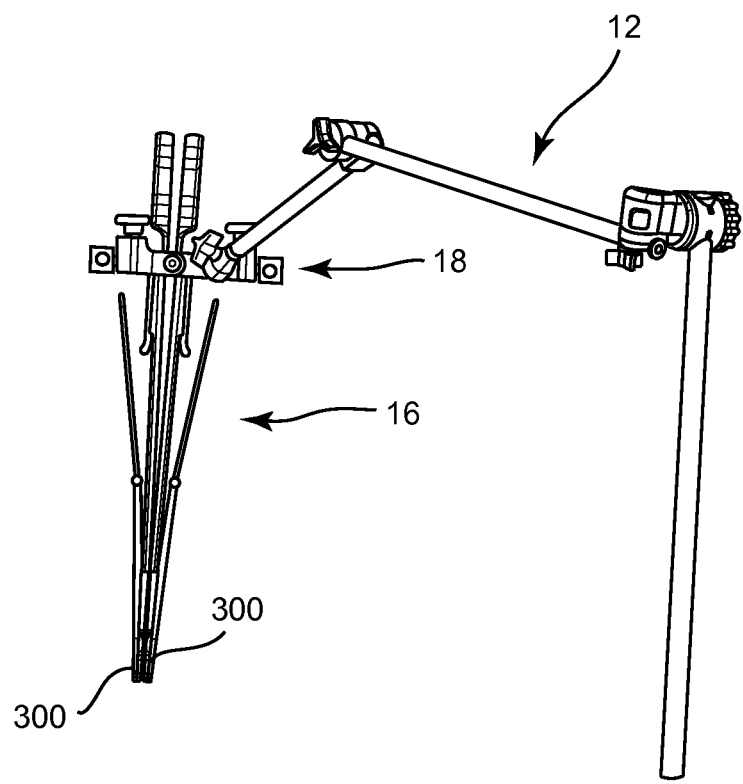
FIG. 2 is a perspective view of an adjustable support assembly, a pivot assembly, and an end plate instrument assembly.

Referring to FIG. 2, a perspective view illustrates two end plates 300 and an end plate instrument assembly 16 necessary to hold and guide the end plates 300 during the implantation process. Also shown are a pivot assembly 18 which holds and adjusts the end plate instrument assembly 16, and an adjustable support assembly 12 which holds the pivot assembly 18. The end plates 300 and the other implant components may be implanted and removed from any one of three approaches: anterior, left lateral or right lateral. Prior to the implantation procedure, the adjustable support assembly 12 is attached to the operating table on the right or left side, depending upon which approach is to be used.

Figure 3:
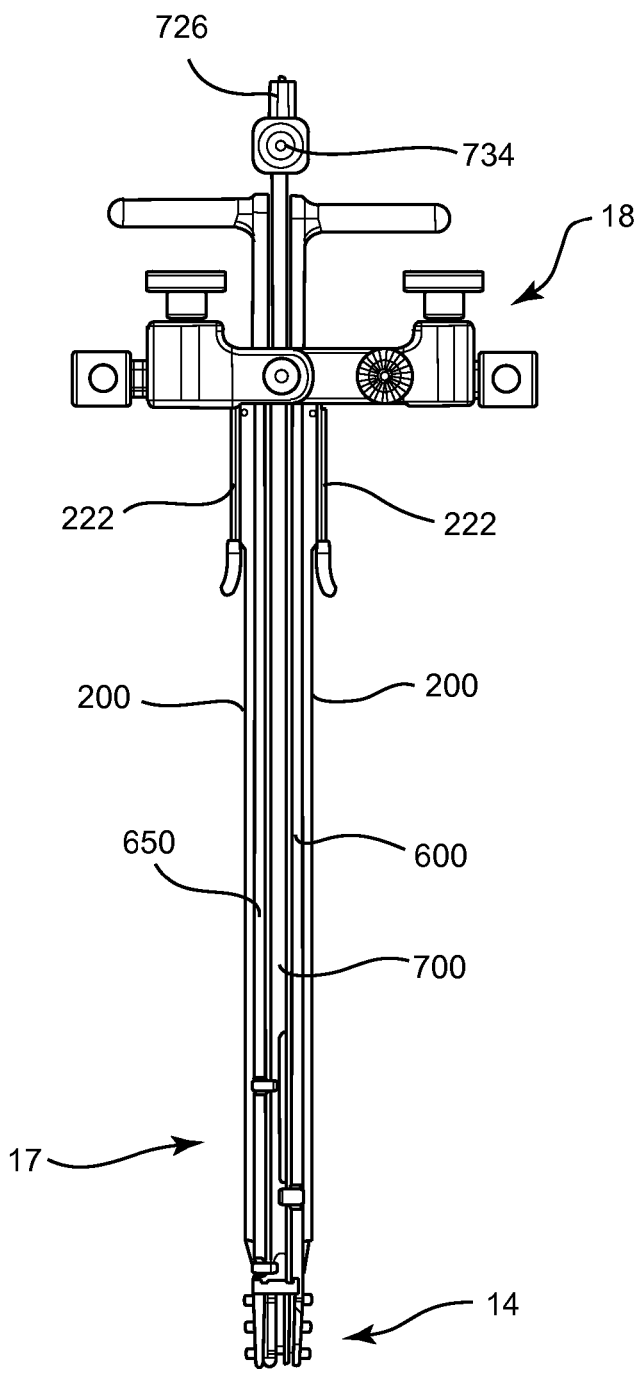
FIG. 3 is a perspective view of a bearing instrument assembly and the pivot assembly shown in FIG. 2, and the implant shown in FIG. 1.

After the end plates 300 are implanted, the inferior 850 and superior bearing 800 are inserted between the end plates. FIG. 3 illustrates a bearing instrument assembly 17 required to insert the bearings. The bearing instrument assembly 17 is supported by the pivot assembly 18, which in turn is held by the adjustable support assembly 12.

The instrumentation illustrated herein is for an implant 14 which has a specific anterior-posterior angle. Implants of differing angulation may be implanted and may require a different configuration of instrumentation. That is, instruments of varying sizes and designs may be necessary to implant an implant of a wider or narrower angle. In addition, the order of the procedure described herein may vary for a different implant.

Figure 4:
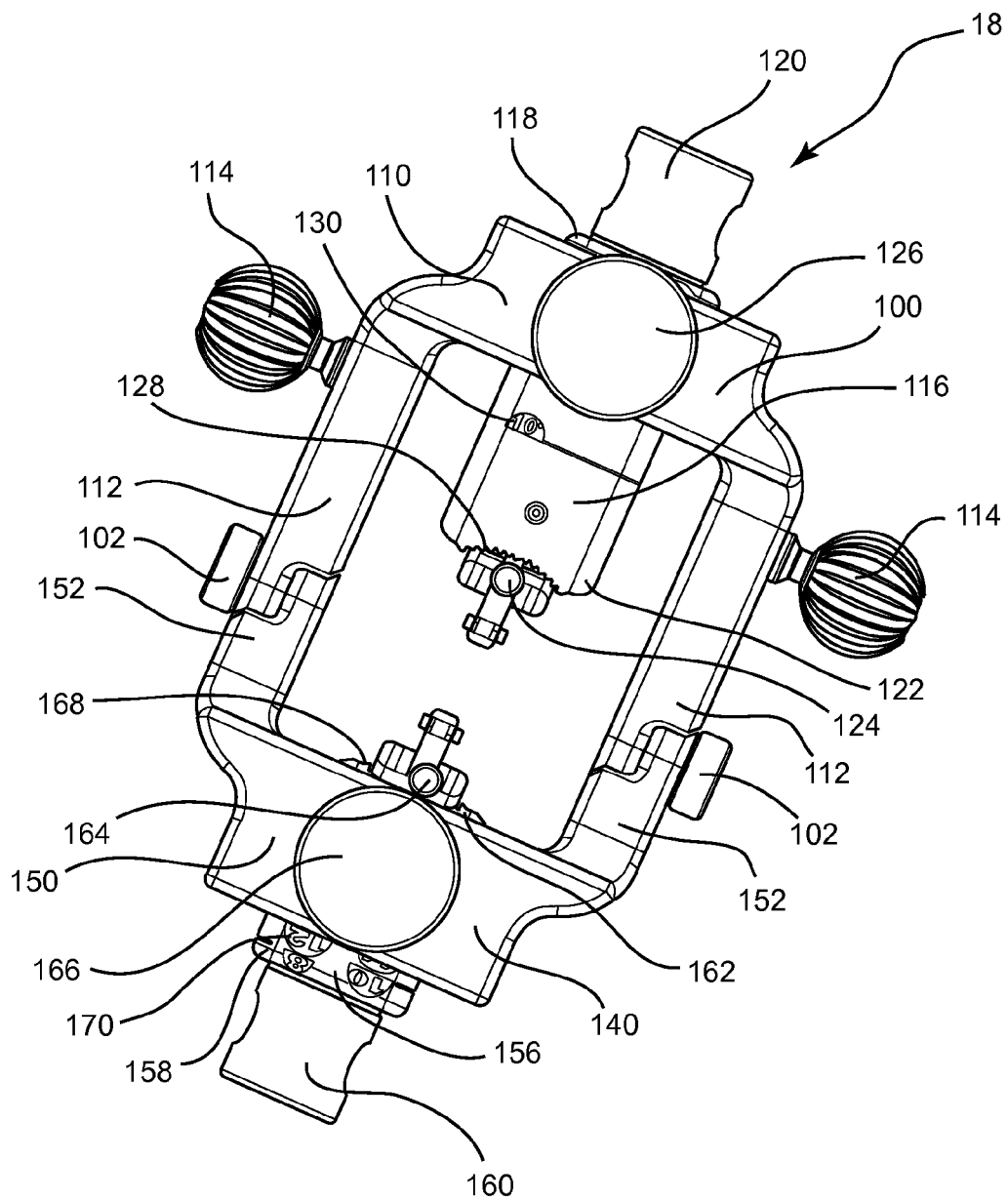
FIG. 4 is a top elevation view of the pivot assembly shown in FIG. 2.

FIG. 4 depicts the pivot assembly 18. The pivot assembly 18 comprises an angle adjustment pivot 100 and a height adjustment pivot 140. The pivots 100, 140 are generally U-shaped and are secured together by two screws 102. The height adjustment pivot 140 has a body 150 and two arms 152 which extend perpendicularly away from the body 150 and parallel to one another, forming a U-shape. The angle adjustment pivot 100 also has a body 110 and two arms 112 which form a U-shape. A support feature in the form of support assembly ball 114 is located on the outer side of each angle adjustment pivot arm 112. The adjustable support assembly 12 depicted in FIG. 2 attaches to the pivot assembly 113 via one of the support assembly balls 114. Which support assembly ball 114 is used is determined by the surgical approach (anterior, right lateral, or left lateral) and the preference of the surgical personnel.

An angle adjustment guide arm 116 extends through in opening in the body 110 of the angle adjustment pivot 100. At the proximal end 118 of the guide arm 116 is an angle adjustment screw 120. This angle adjustment screw 120 extends through the length of the guide arm 116 and emerges at the distal end 122 of the guide arm 116, and is capped by an adjustment nut 124. An angle adjustment gauge 130 appears as a series of numbers on the top side of the body 110. Also on the top side of the body 110, an adjustment knob 126 extends through an opening in the body 110 to the top of the angle adjustment guide arm 116. Tightening the adjustment knob 126 secures the angle adjustment guide arm 116 in place within the angle adjustment pivot 100. A row of angle guide arm teeth 128 line the distal end 122 of the angle adjustment guide arm 116.

A height adjustment guide arm 156 extends through an opening in the body 150 of the height adjustment pivot 140. At the proximal end 158 of the guide arm 156 is a height adjustment screw 160. This height adjustment screw 160 extends through the length of the guide arm 156 and emerges at the distal end 162 of the guide arm 156, and is capped by an adjustment nut 164. A height adjustment gauge 170 appears as a series of numbers on the top side of the body 150. Also on the top side of the body 150, an adjustment knob 166 extends through an opening in the body 150 to the top of the height adjustment guide arm 156. Tightening the adjustment knob 166 secures the height adjustment guide arm 156 in place within the height adjustment pivot 140. A row of height guide arm teeth 168 line the distal end 162 of the height adjustment guide arm 156.

Figure 5:
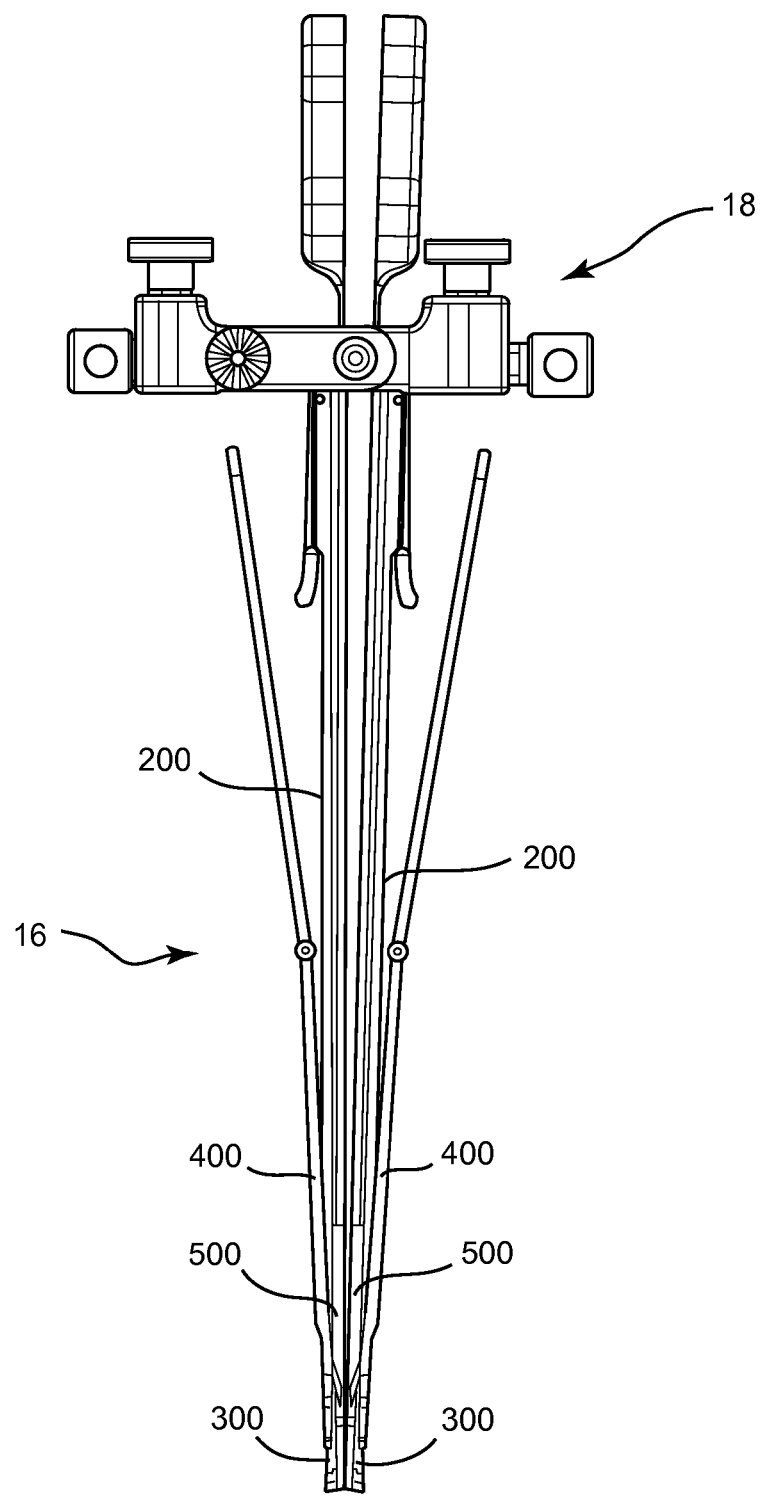
FIG. 5 is a perspective view of the end plate instrument assembly and the pivot assembly shown in FIG. 2, and two end plates.

The instrument assembly 16 and pivot assembly 18 are depicted in FIG. 5. Individual components of the instrument assembly 16 are positioned, implemented, and removed throughout the implantation procedure. In the embodiment depicted, the instrument assembly 16 consists of two end plate holders 200, two spike guards 400, and two primary spacers 500. Attached to the distal end of the end plate holders 200 are two end plates 300. (Additional spacers not depicted in FIG. 5 are used in the procedure and will be illustrated and described as they are used.)

Figure 6:
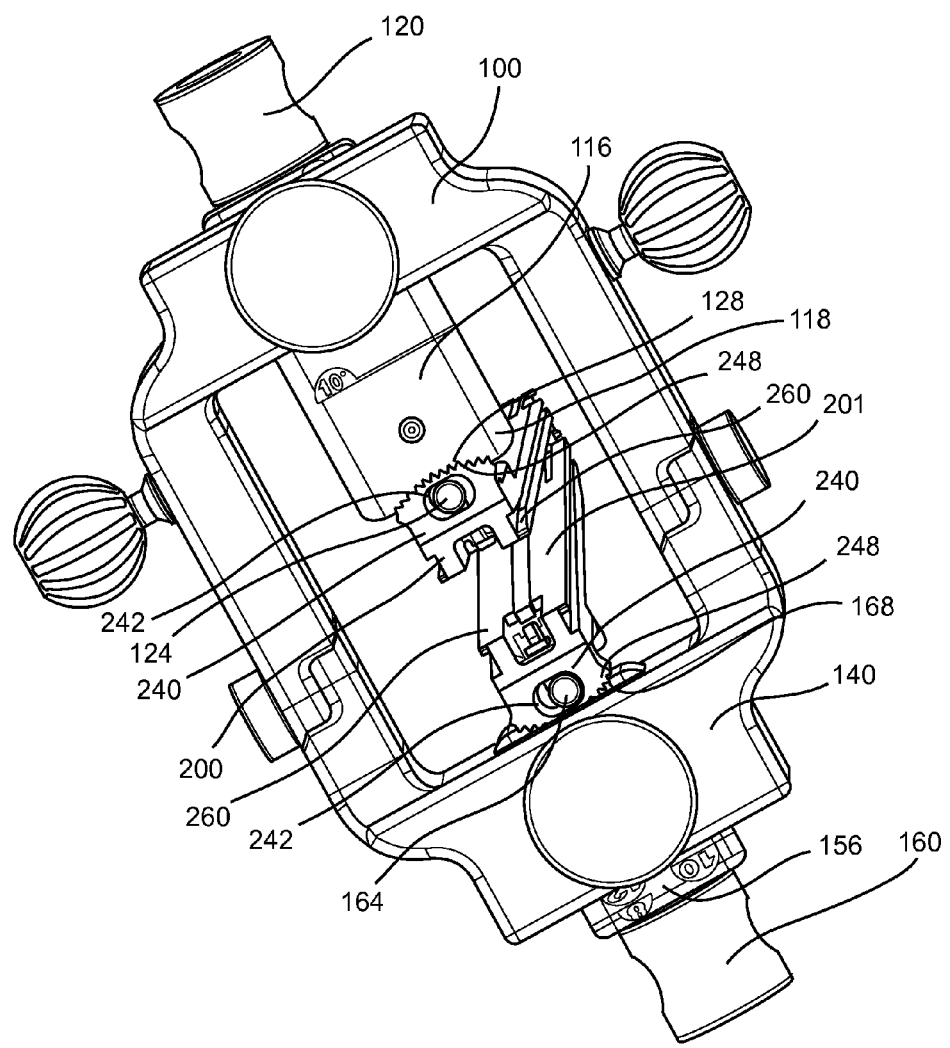
FIG. 6 is a perspective view of the pivot assembly shown in FIG. 2 and two end plate holders.

FIG. 6 depicts a top-down view of the pivot assembly 18 and its connection to the end plate holders 200. The two end plate holders 200 are identical to one another; they differ only in orientation during the implantation procedure. Each end plate holder 200 has a distal first end 250 and a proximal second end 260, connected by a shaft 201. At the second end 260 of each end plate holder 200 is a connector 240 with an opening 242 and a plurality of connector teeth 248. One end plate holder is connected to the height adjustment guide arm 156 by fitting the opening 242 over the adjustment nut 164, and meshing the connector teeth 248 with the height guide arm teeth 168. The other end plate holder 200 is connected to the angle adjustment guide arm 116 in an identical manner; by fitting the opening 242 over the adjustment nut 124, and meshing the connector teeth 248 with the angle guide arm teeth 128. Once the end plate holders 200 are connected to the adjustable guide arms 116, 156, the height of the end plate holders 200 can be adjusted by turning the height adjustment screw 160, and the angle of the end plate holders 200 can be adjusted by turning the angle adjustment: screw 120.

Figure 7:
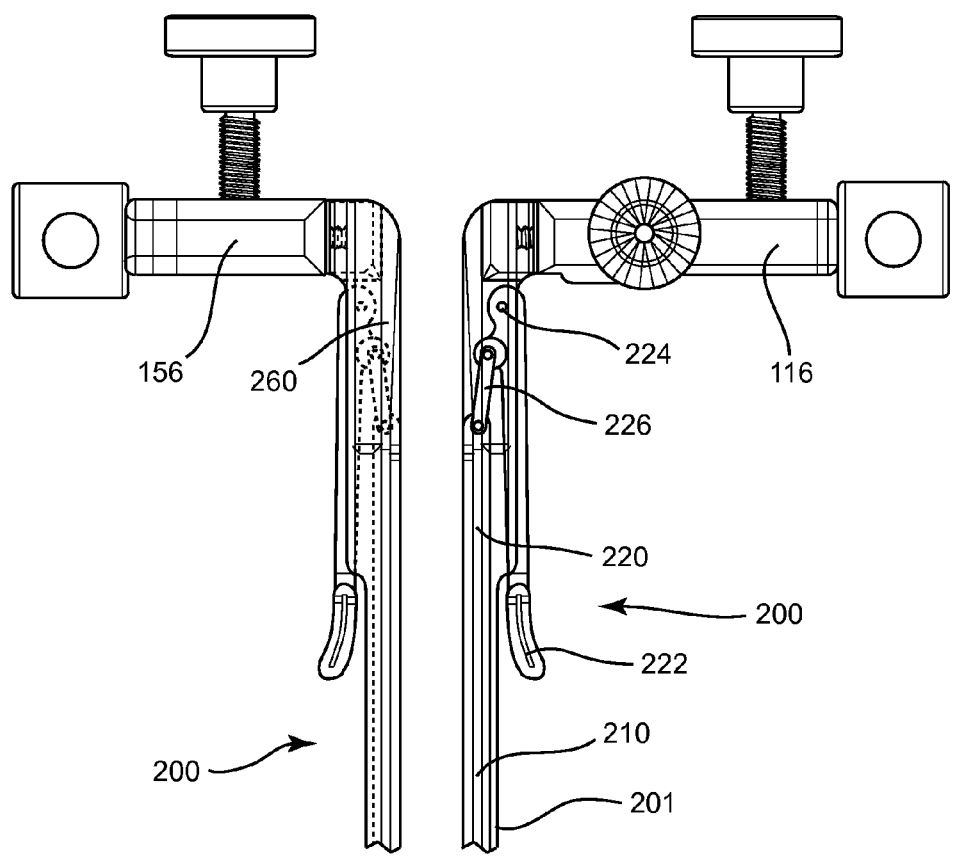
FIG. 7 is a side elevation view of the pivot assembly and end plate holders shown in FIG. 6, with hidden parts shown in phantom.

A transparent side view of the proximal end of the end plate holders 200 and the guide arms 116, 156 is shown in FIG. 7. Fitted into a longitudinal channel 210 in each shaft 201 is a spreader 220. The spreaders 220 lie on the inside planes of the end plate holders 200 such that the spreaders 220 face one another once the end plate holders 200 are secured to the adjustment arms 116, 156. Each spreader 220 has a lever 222 which lies on the outside of the end plate holder 200. A rod 226 and lever pin 224 assembly connect the spreader 220 to the lever 222. When the lever 222 is in the lowered position as in FIG. 5, the spreader 220 is extended distally down the channel 210 of the shaft 201.

Figure 8:
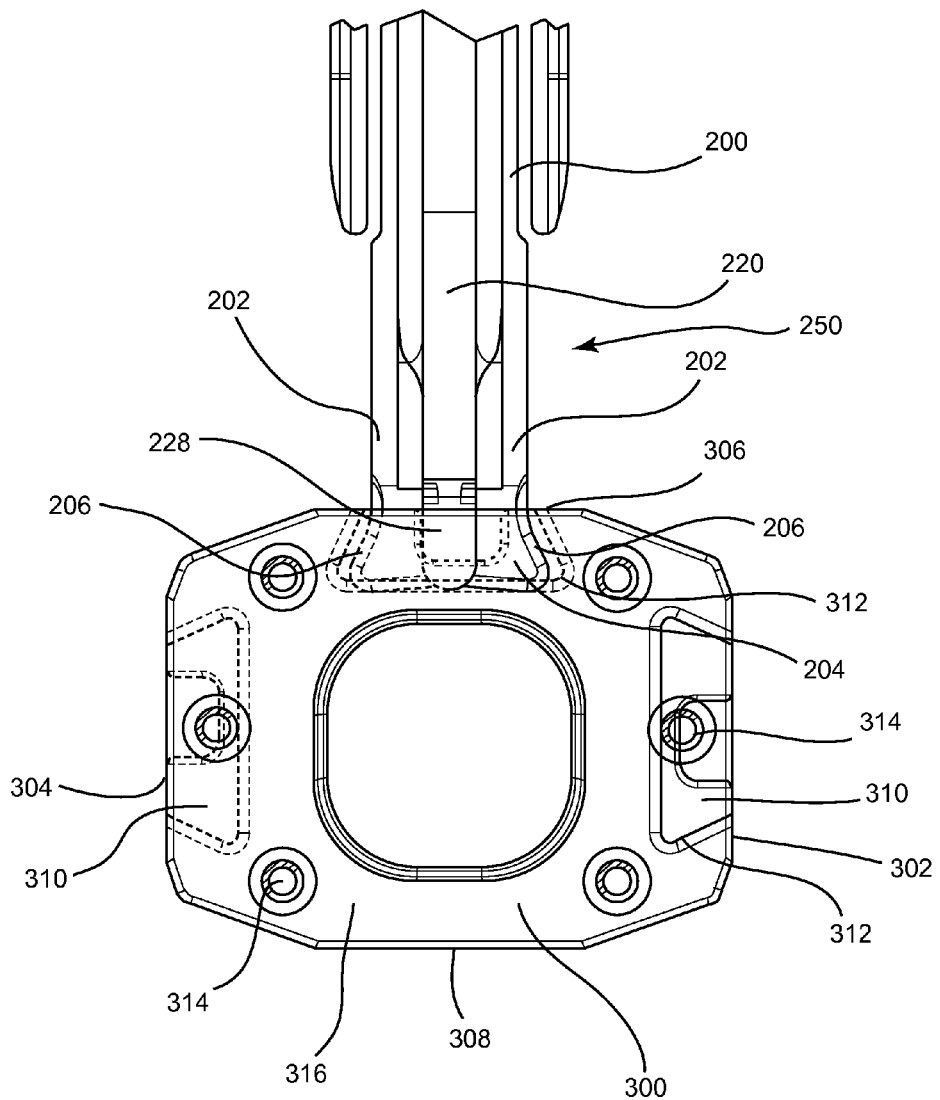
FIG. 8 is a side elevation view of the distal end of an end plate holder shown in FIG. 6 and an end plate, with hidden parts shown in phantom.

An end plate 300 and its connection to the first end 250 of the end plate holder 200 are illustrated in FIG. 8. The end plate 300 has a right lateral end 302, a left lateral end 304, an anterior end 306 and a posterior end 308. The end plate 300 has three pockets 310, placed on the right lateral end 302, the left lateral end 304, and the anterior end 306. The three pockets 310 are identical in shape and design, only differing in placement on the end plate 300. Each pocket 310 has two angled corners 312. If the implant 14 is to be placed using the anterior approach, as depicted in FIG. 8, the end plate holder 200 will be connected to the end plate 300 via the pocket 310 located on the anterior end 306. Similarly, if the implant 14 is to be placed using a right lateral approach, the end plate holder 200 will be connected via the pocket 300 on the right end 302 and if the implant is to be placed using a left lateral approach, the end plate holder 200 will be connected via the pocket 310 in the left end 304.

The first end 250 of the end plate holder 200 comprises an expandable retention interface having two prongs 202. The two prongs 202 terminate in angled prong tips 204, which have radius edges 206. In the embodiment depicted, the anterior approach is used, so the end plate holder 200 is connected to the end plate 300 by placing the two prongs 202 into the pocket 310 on the anterior end 306. Once the prongs 202 are placed in the pocket 310, the spreader 220 is extended lengthwise between the two prongs 202, by lowering the lever 222 illustrated in FIG. 7. As the spreader 220 extends, the prong tips 204 are forced apart, and pushed into the outer pocket corners 312. When the spreader 220 is filly extended, the spreader tip 228 is pushed firmly against the end of the pocket 310, and the prong tips 204 are forced slightly back, thus seating their rounded edges 206 against the pocket corners 312. This seating creates a firm connection between the end plate 300 and the end plate holder 200. The second end plate 300 is connected to the first end 250 of the second end plate holder 200 in an identical manner.

As seen in FIG. 8, each end plate 300 has a plurality of spikes 314. The spikes 314 comprise hollow, pointed protrusions extending from an exterior surface 316 of the end plate 300. The spikes 314 are positioned such that they form a ring on the exterior surface 316, but are set back from the ends 302-308 of the end plate 300, allowing an outer ring of flat surface area between the spikes 314 and the ends 302-308.

Figure 9:
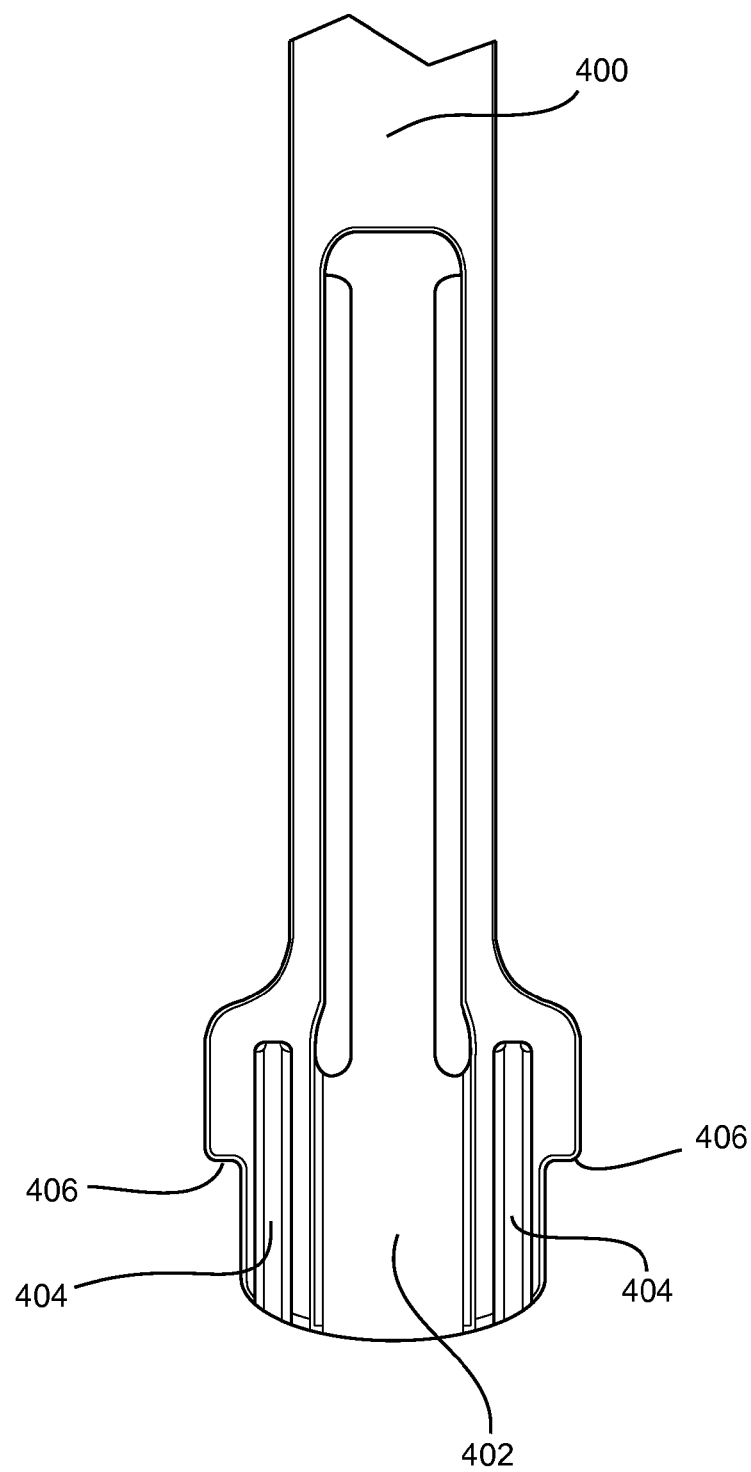
FIG. 9 is a side elevation view of the distal end of a spike guard.
Figure 10:
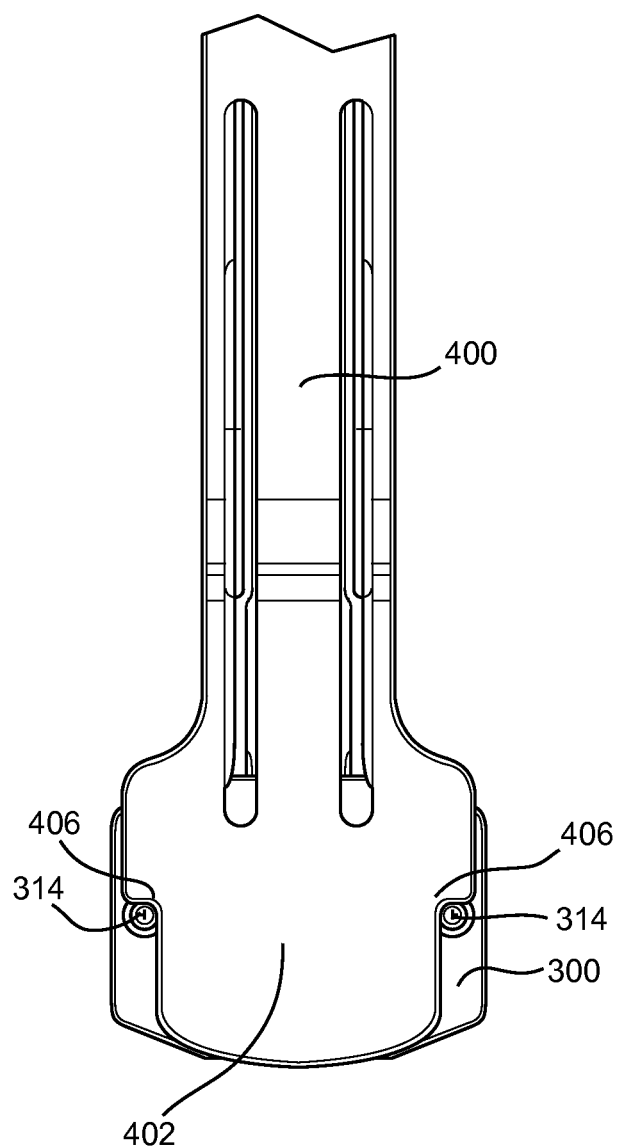
FIG. 10 is a side elevation view of the distal end of the spike guard shown in FIG. 9 mounted on an end plate.

After each of the end plates 300 is attached to the end plate holders 200, a spike guard 400 is fitted over the exterior surface 316. As seen in FIG. 9, the distal end of each spike guard 400 terminates in a flat, spatula-like cover plate 402 that fits over the exterior surface 316 of the end plate 300. The inside of the cover plate 402 has grooves 404 into which the centrally located spikes 314 slide as the spike guards 400 are put on. The spike guards 400 are put on to the end plates 300 by sliding them distally parallel to the end plate holders 200 and onto the end plates, allowing the spikes 314 to slide into the grooves 404, illustrated in FIG. 10. The outer surface of the cover plate has two curved notches 406 which come to rest around the spikes 314 nearest the right end 302 and left end 304 of the end plate 300. These two spikes 314 are not covered, but the outer surface of the cover plate 402 extends higher than the ends of the spikes 314, so the spikes 314 do not protrude past the cover plate 402. The cover plate 402 prevents the spikes 314 from snagging or scratching anything prior to implantation, and prevents premature contact between the spikes 314 and the vertebral bodies. The spike guards 400 are composed of a radiolucent material, so that the end plates 300 are visible through radiography during the implantation process. Placement and removal of the spike guards 400 is via handles (not visible in FIG. 9). The spike guard depicted in FIGS. 9 and 10 is designed for use during an anterior approach implantation. It is appreciated that the shape and placement of the spike guards may differ in alternative embodiments of the invention.

Figure 11:
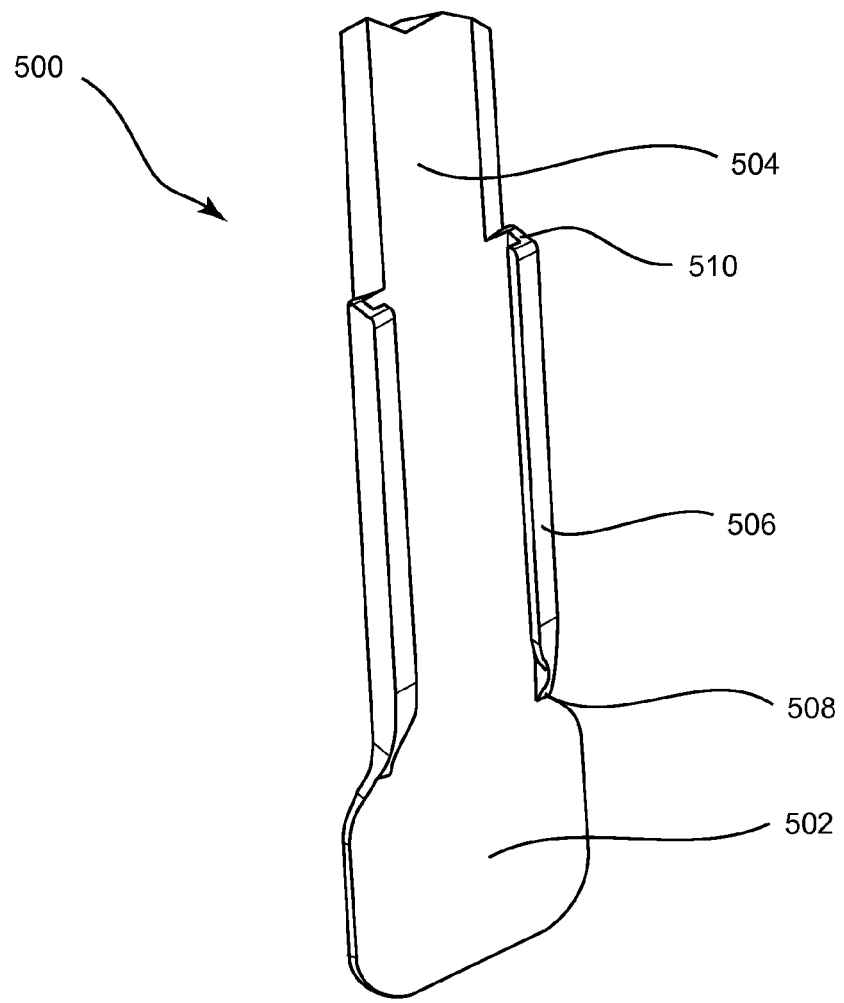
FIG. 11 is a perspective view of the distal end a primary spacer.

FIG. 11 depicts the distal end of a primary spacer 500. The distal end of the primary spacer 500 terminates in a flat, rectangular plate 502. A shaft 504 connects the plate 502 to a handle at the proximal end (not visible in FIG. 11). Raised edges 506 extend partway up the shaft 504 from the plate 502 toward the proximal end The raised edges 506 have a distal end 508 near the plate 502 and a proximal end 510 partway up the shaft 504.

Figure 12:
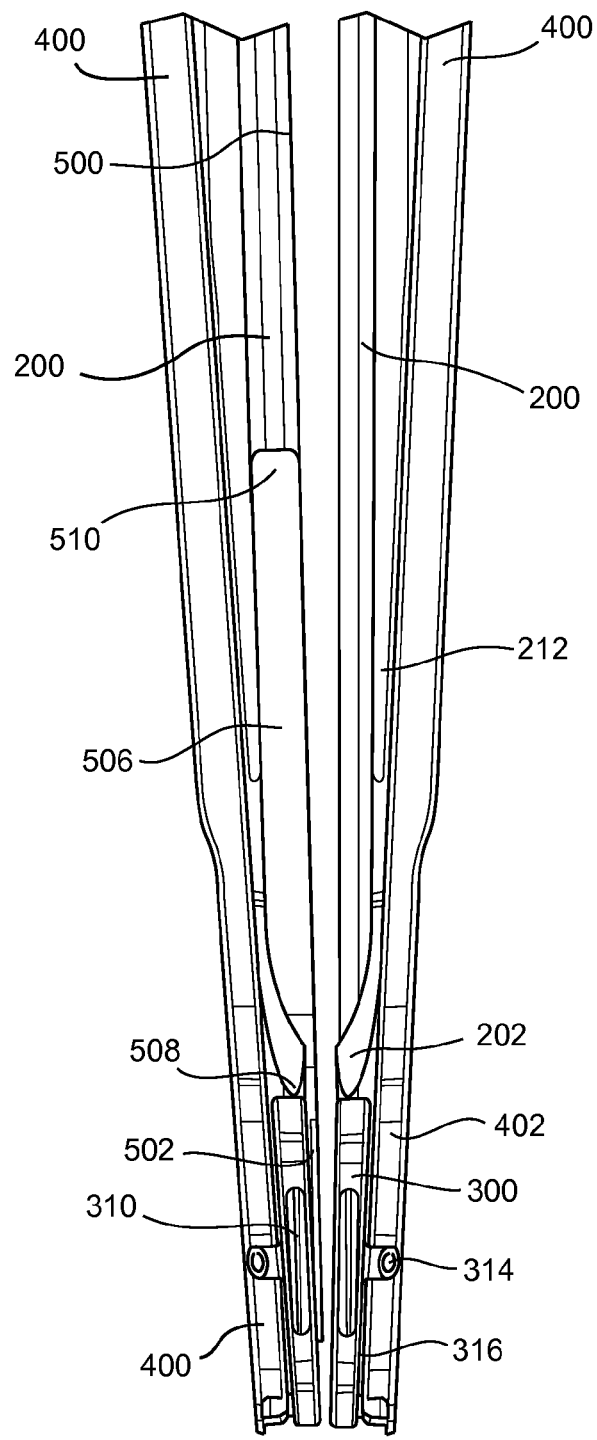
FIG. 12 is a side elevation view of the end plate instrument assembly shown in FIG. 5, and two end plates.

FIG. 12 illustrates the distal ends of the two end plate holders 200 with attached end plates 300, spike guards 400, and one primary spacer 500. Two primary spacers 500 are used in the procedure, but only one is illustrated so that the details of the end plate holder 200 may be seen. Either before or after the spike guards 400 are fitted over the end plates 300, the two primary spacers 500 are slid in between the end plate holders 200, as also shown in FIG. 5. The first primary spacer 500 is slid parallel to the inner side of the end plate holder 200 such that the raised edges 506 clasp around the lateral edges of the end plate holder 200 and slide inside a lateral groove 212. When the distal end 508 of the raised edge 506 contacts the end plate 300, the primary spacer 500 is in place and cannot move distally any more. The plate 502 is in between the two end plates 300. The other primary spacer 500 is slid into place next to the other end plate holder 200, and its plate 502 comes to rest between the first plate 502 and the end plate 300. The primary spacers are radiolucent, so they do not obscure the visibility of the end plates 300 and vertebral bodies during implantation. The number and positioning of spacers may vary with alternative embodiments of the invention.

The pivot assembly 18 and attached instrument assembly 16 are now ready to be positioned for the implantation procedure. Referring to FIGS. 2, and 4, the pivot assembly 18 is attached to the adjustable support assembly 12 via one of the two support assembly balls 114. The support assembly 12 is adjusted so that the pivot assembly 18 and the instrument assembly 16 are supported over the patient in a position appropriate to the approach chosen (anterior, right lateral, or left lateral). The instrument assembly 16 is positioned so that the end plates 300 covered with the protective spikes guards 400 are placed between the vertebral bodies. Radiography is employed to observe the positioning of the end plates. At this point, the surgical personnel select the components of the disc implant 14. The radiolucent spike guards 400 allow the surgical personnel to see the end plates 300 in position relative to the vertebral bodies, and the personnel can determine which size, thickness and angle of bearings 800, 850 should be used.

Figure 13:
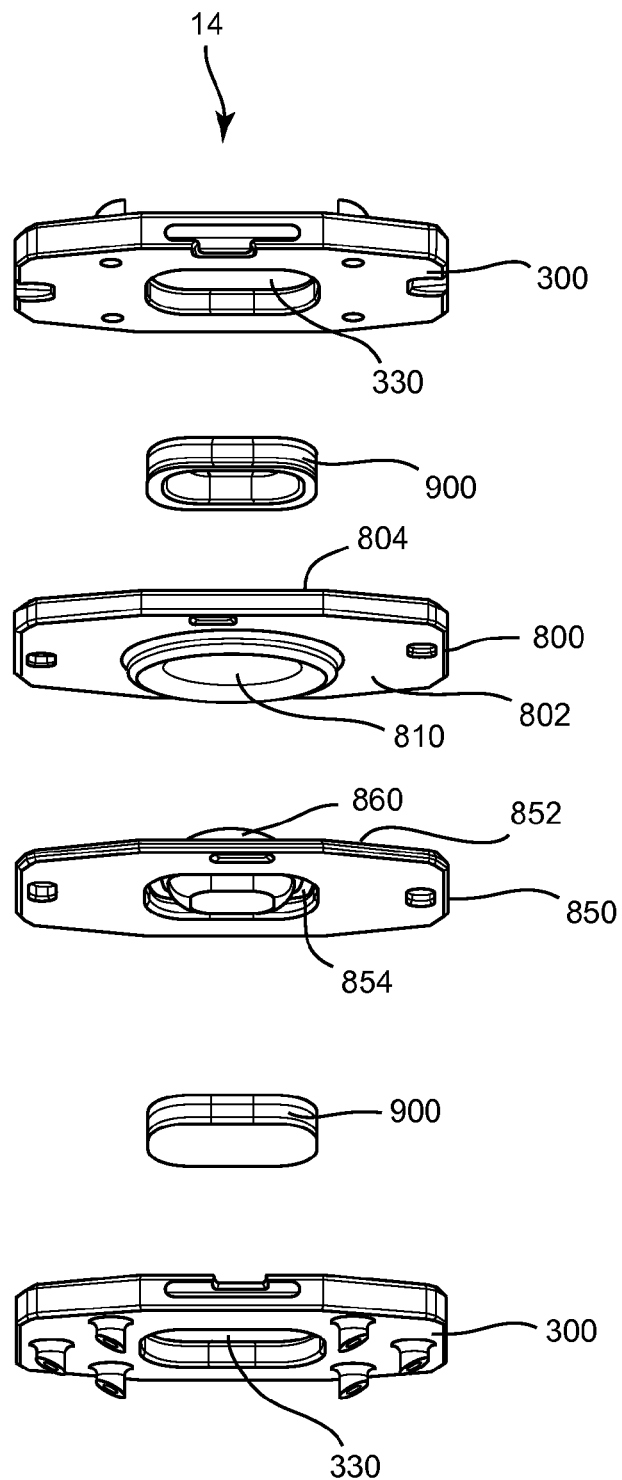
FIG. 13 is a perspective view of an intervertebral disc motion preservation implant in a disassembled state.

FIG. 13 displays an exploded side view of disc implant 14. The superior bearing 800 has a superior bearing surface 802 in which is an indented cup 810. The inferior bearing 850 has an inferior bearing surface 852, from which protrudes a dome 860. When the bearings 800, 850 are held in place between the two end plates 300, the cup 810 fits over the dome 860, and the superior bearing surface 802 is in contact with the inferior bearing surface 852. The snap fasteners 900 connect the bearings 800, 850 to the end plates 300 by fitting into snap ports 330 on the end plates 300, and into troughs 804, 854 on the bearings 800, 850.

All pieces—end plates 300, the inferior bearing 850, the superior bearing 800 and the snap fasteners 900 are made in three sizes, where size refers to the area of the component, which will correspond to the area of the vertebral bodies where the disc implants are implanted. The superior bearings 800 are made in a variety of thicknesses, to match the height of the intervertebral space. The inferior bearings 850 are made in a variety of angles, in which the height of the posterior end of the inferior bearing is greater than the height of the anterior end of the inferior bearing, to match the angle of the intervertebral space. If deemed necessary, the end plates 300 can be removed and alternate, differently sized end plates 300 substituted for them.

Referring back to FIG. 6, the adjustment screws 160, 120 on the guide arms 156, 116 allow for height and angle adjustment control at the second ends 260 of the end plate holders 200 while the first ends 250 are inserted in the intervertebral space. The height adjustment screw 160 at the second end 260 of the end plate holder 200 can be turned in either direction, raising or lowering the first end 250 of the end plate holder 200, until the end plate 300 is correctly positioned in the intervertebral space. The height measurement gauge 170 is read on the height adjustment guide arm 156 and the superior bearing 800 matching that height is selected. Similarly, the angle adjustment screw 120 at the second end 260 of the other end plate holder 200 can be turned, changing the anterior-posterior angle of the first end 250 of the other end plate holder 200, until the end plate 300 is correctly positioned. The angle measurement gauge 130 is read on the angle adjustment guide arm 116 and the inferior bearing 850 matching that angle is selected.

An alternate method for determining the correct size of end plates 300 and bearings is to have a group of samples which duplicate the size, thickness and angles of the end plates and bearings. These sample components are each mounted on a shaft to allow temporary insertion into the intervertebral space, to determine if the size, thickness and angle of the components are correct. A sample has the same dimensions as the two end plates, the inferior and superior bearings, and the snap fittings do when they are fitted together as they would be in the intervertebral space. Instead of temporarily inserting and removing the actual end plates and bearings to check for the proper configuration, the samples can be inserted and removed to determine the proper choice for each component.

Once the correct disc implant 14 components are chosen, the final position of the end plates 300 is adjusted. Radiography is used to see where the end plates 300 and more specifically the spikes 314 will fit against the vertebral bodies. The angle adjustment screw 120 is turned to place the end plate holder 200 and end plate 300 at the proper angle. The height adjustment screw 160 is turned to raise or lower the other end plate holder 200 and end plate 300. Once the correct angle and height are determined, the adjustment knob 126 is tightened to lock the angle adjustment guide arm 116 in place, and the adjustment knob 166 is tightened to lock the height adjustment guide arm 156 in place.

Figure 14:
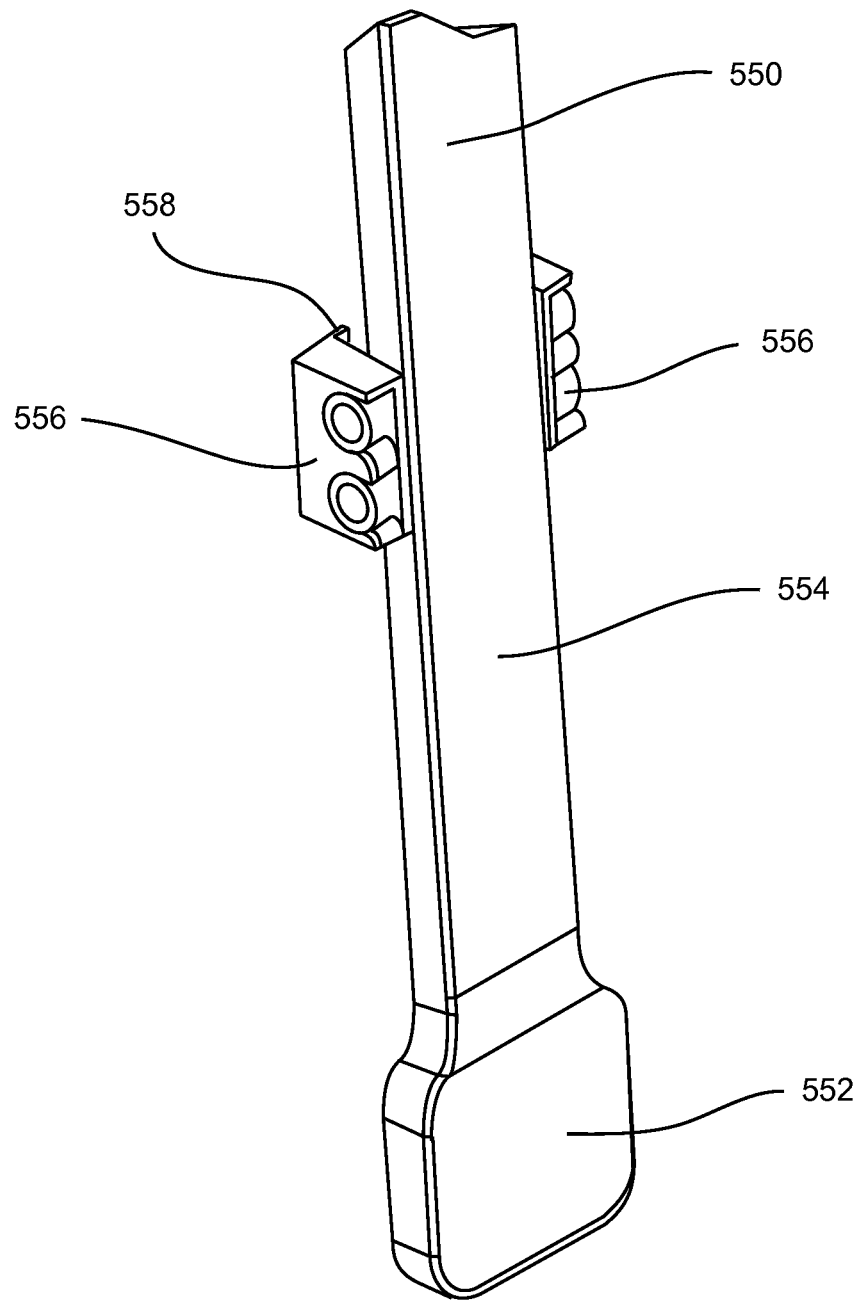
FIG. 14 is a perspective view of the distal end of a secondary spacer.

With the end plate holders 200 now locked in place at the correct height and angle, the spike guards 400 are removed, allowing the now exposed spikes, 314 to engage against the surface of the vertebral bodies. Secondary spacers 550 are inserted between the primary spacers 500. This action pushes the end plates 300 cephalic-caudally away from one another, and presses the spikes 314 into the vertebral bodies. FIG. 14 illustrates the distal end of an individual secondary spacer 550. The secondary spacer 550 terminates in a paddle-like plate 552 that is thicker than the plate 502 of the primary spacer 500. A shaft 554 connects the plate 552 to a handle (not visible in FIG. 14). Partway up the shaft 554 in a proximal direction from the plate 552, a pair of rails 556 are on either side of the shaft 554. The rails 556 have squared edges 558 which extend out from the shaft 554.

Figure 15:
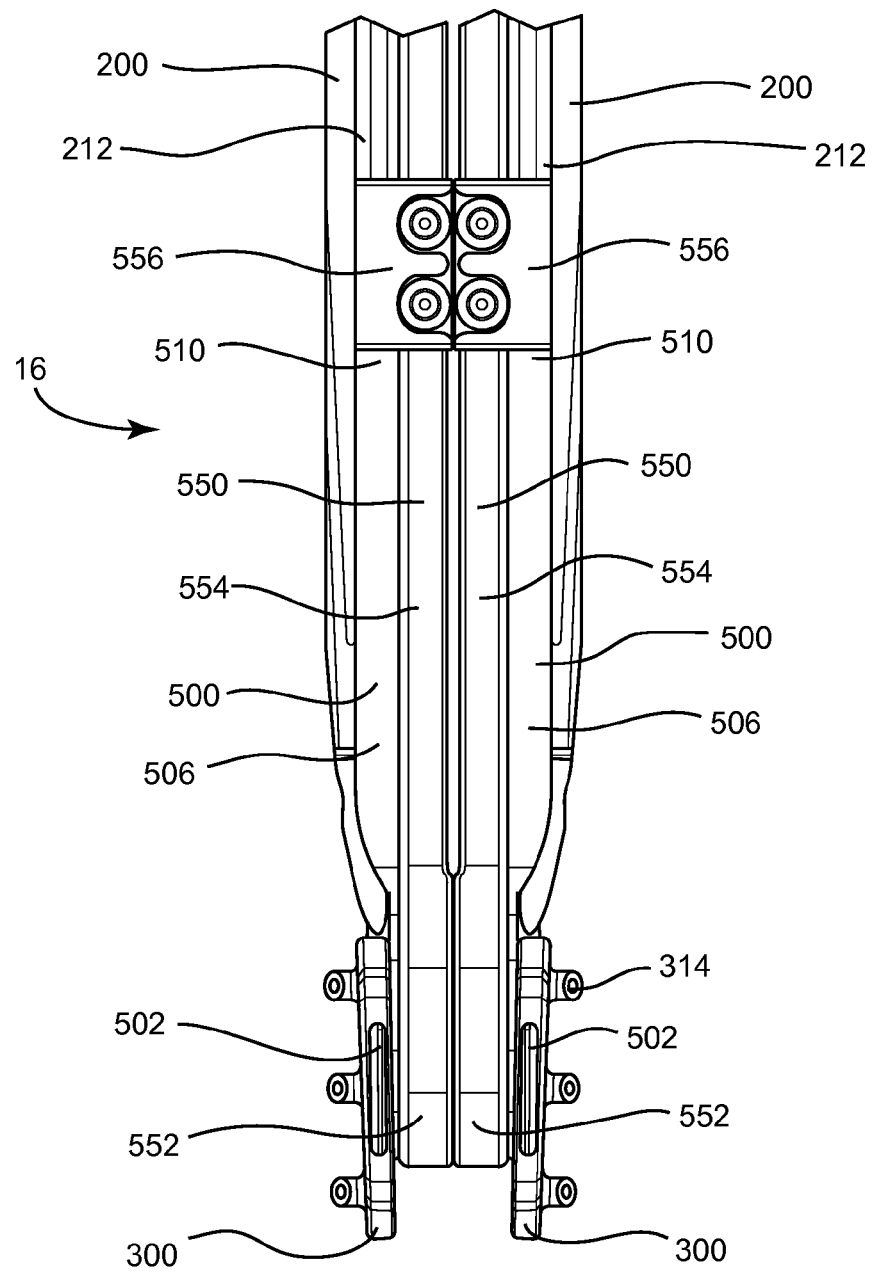
FIG. 15 is a side elevation view of the distal end of two end plate holders and end plates shown in FIG. 8, and two primary spacers shown in FIG. 12, and two secondary spacers shown in FIG. 14.

FIG. 15 illustrates the distal end of instrument assembly 16, including end plate holders 200, and primary and secondary spacers 500, 550. The end plate holders 200 are holding two end plates 300. The secondary spacers 550 are inserted one at a time into the space between the two primary spacers 500. As the secondary spacer 550 is moved into place, the edges 558 of the rails 556 slide into the lateral grooves 212 on the end plate holder 200. The secondary spacer 550 is slid distally until the rails 556 contact a proximal end 510 of the raised edges 506 of the primary spacer 500, preventing the secondary spacer 550 from sliding any further. The plate 552 is now positioned next to the plate 502 of the primary spacer 500, and the primary spacer 500 is sandwiched between the end plate holder 200 and the secondary spacer 500. The other secondary spacer 550 is inserted in the same fashion onto the opposite primary spacer 500 and end plate holder 200. The action of inserting the secondary spacers 550 pushes the spikes 314 into the vertebral bodies, thus firmly seating the exterior surfaces 316 of the end plates 300 against the surface of the vertebral bodies.

With the end plates 300 implanted in the vertebral bodies, the primary spacers 500 and secondary spacers 550 are removed. Removal is accomplished by grasping the handles of the spacers 500, 550 and pulling them proximally until they are free of the instrument assembly 16.

Referring back to FIG. 3, the bearing instrument assembly 17 used to place the bearings 800, 850 between the implanted end plates 200 is depicted. This assembly is supported by the pivot assembly 18, and comprises the end plate holders 200, an angle compressor 650, a height compressor 600, and a bearing holder 700. At the distal end of the instrumentation set is the intervertebral disc motion preservation implant 14, which comprises the two end plates 300, an inferior bearing 800, a superior bearing 850, and two snap fasteners 900, as illustrated in FIG. 10. The instruments which comprise instrument assembly 17 are assembled in the following order: the angle compressor 650 is inserted between the end plate holders 200; the bearings 800, 850 are attached to the bearing holder 700; the height compressor 600 is attached to the bearing holder 700; and the bearing holder 700 (with attached height compressor 600 and bearings 800, 850) is inserted between the end plate holders 200.

Figure 16:
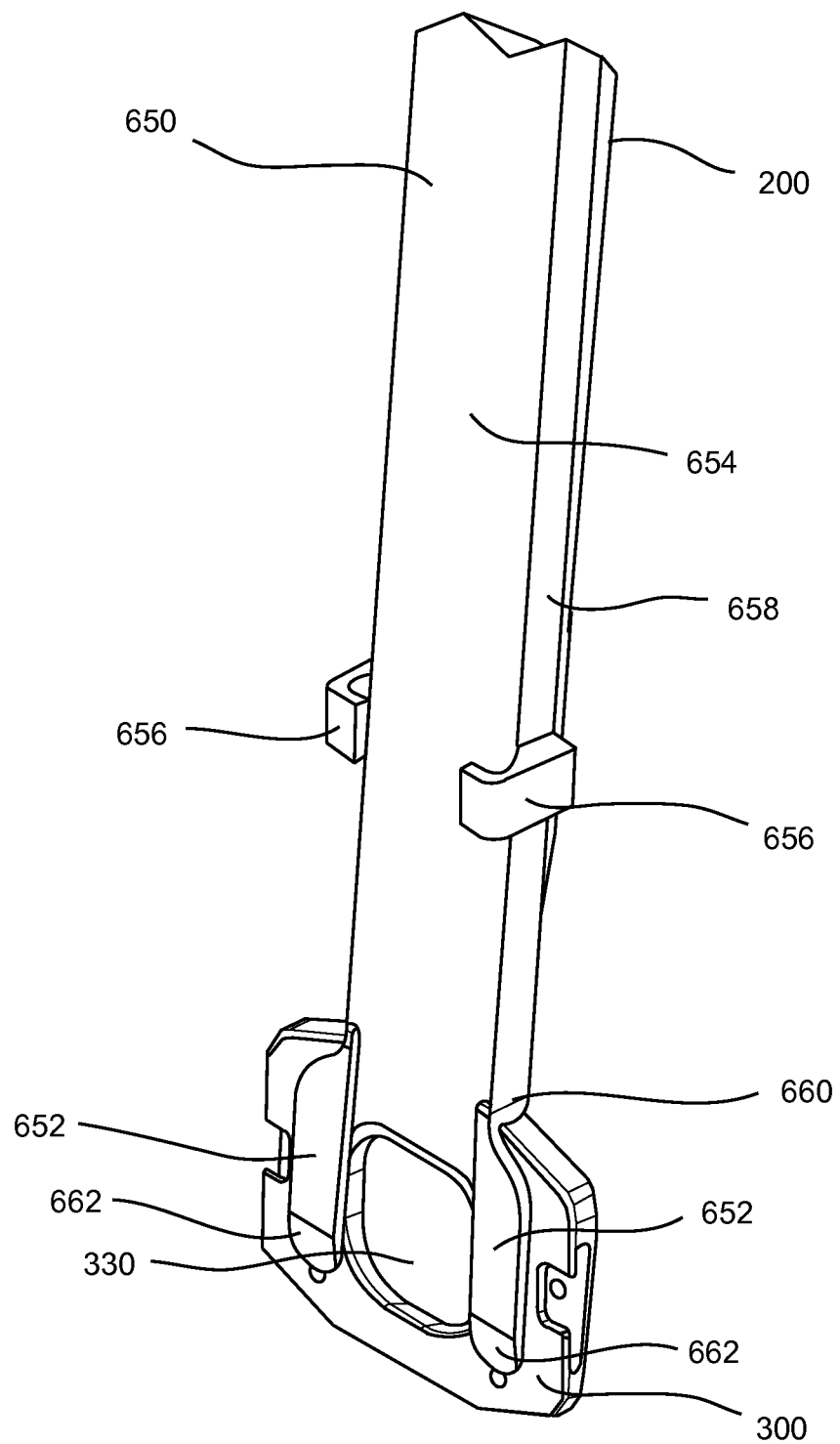
FIG. 16 is a perspective view of the distal end of an angle compressor and an end plate.

FIG. 16 depicts the distal end of one angle compressor 650 with one end plate holder 200 and one end plate 300. The angle compressor 650 is comprised of a handle at the proximal end (not visible in FIG. 14), a shaft 654, and two prongs 652. The shaft 654 has raised edges 658 which extend perpendicularly from the shaft 654 and bend to form an L-shape. At the distal end of the shaft 654 are the prongs 652 which each terminate in an angled ramp 662. Partway up the shaft 654 in a proximal direction are a pair of rails 656. The L-shaped rails 656 extend in the opposite direction from the raised edges 658. The angle compressor 650 is slid onto the end plate holder 200 which is attached to the angle guide arm 116 as seen in FIG. 6. The raised edges 658 slide into the lateral grooves 212 on either side of the end plate holder 200. The angle compressor 650 is slid distally down the length of the end plate holder 200 until the distal ends 660 of the raised edges 658 contact the end plate 300. The prongs 652 lie on either side of the snap port 330 of the end plate 300.

Figure 17:
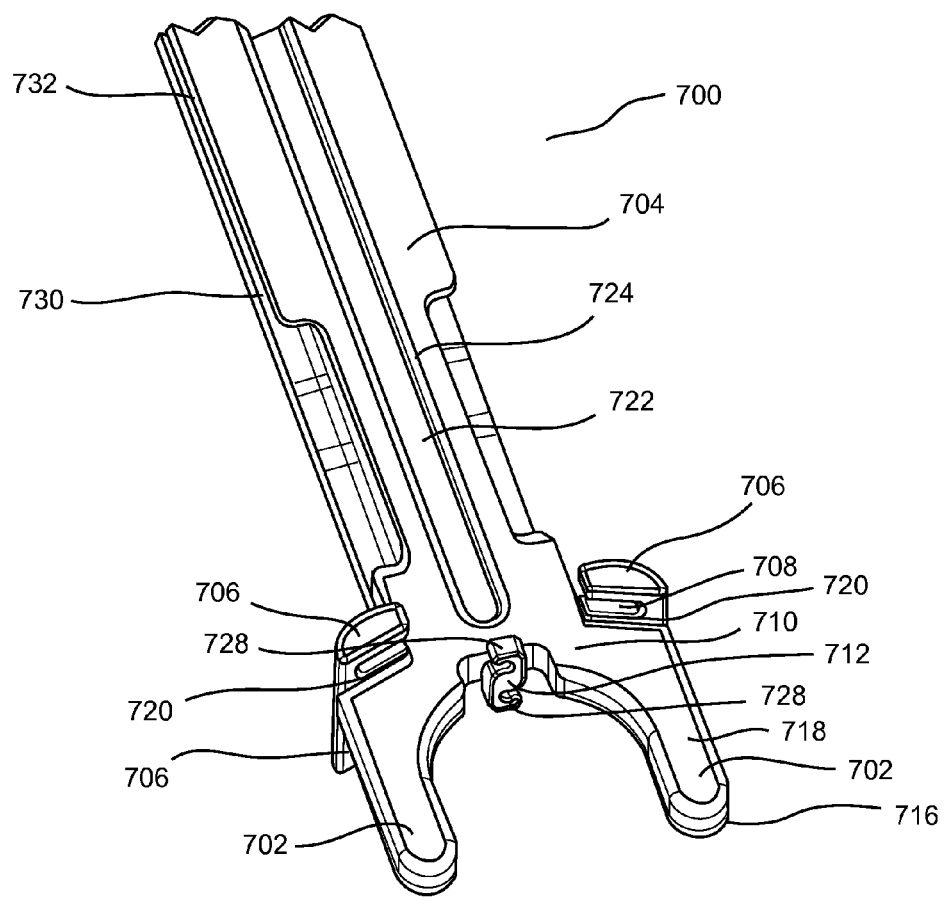
FIG. 17 is a perspective view of the distal end of a bearing holder.

The inferior side of the distal end of bearing holder 700 is illustrated in FIG. 17. The bearing holder 700 has two handles 734 at the proximal end (visible in FIG. 3), and a shaft 704 which terminates at its distal end all an intersection with a body 710. Along each lateral side of the shaft 704 is a camming channel 730 with undulating edges 732. The body 710 extends distally and splits into two prongs 702. The body 710 and prongs 702 are generally flat and fork-like in shape, with a superior side 716 and an inferior side 718. Where the body 710 originates at the base of the shaft 704 are two shoulders 706, one on each lateral side of the shaft 704. Each shoulder 706 extends perpendicularly from the body 710 in both directions. On each side of each shoulder is a slot 708 which lies parallel to the prongs 702 and is open to the inside of the shoulder 706 adjacent to the shaft 704. At the base of each shoulder 706, and between the slot 708, and the body 710, is a slanted edge 720.

Where the two prongs 702 meet at the base of the body 710 is a locking key 712 with two teeth 728. The locking key 712 is mounted on the end of a pin 722 that extends from the proximal end of the shaft to the distal end, and is enclosed in a channel 724. At the proximal end of the bearing holder 700, the pin 722 emerges from the channel 724 and is capped by an adjustment nut 726 (seen in FIG. 3). When the adjustment nut 726 is turned, the pin 722 and the locking key 712 turn.

Figure 18:
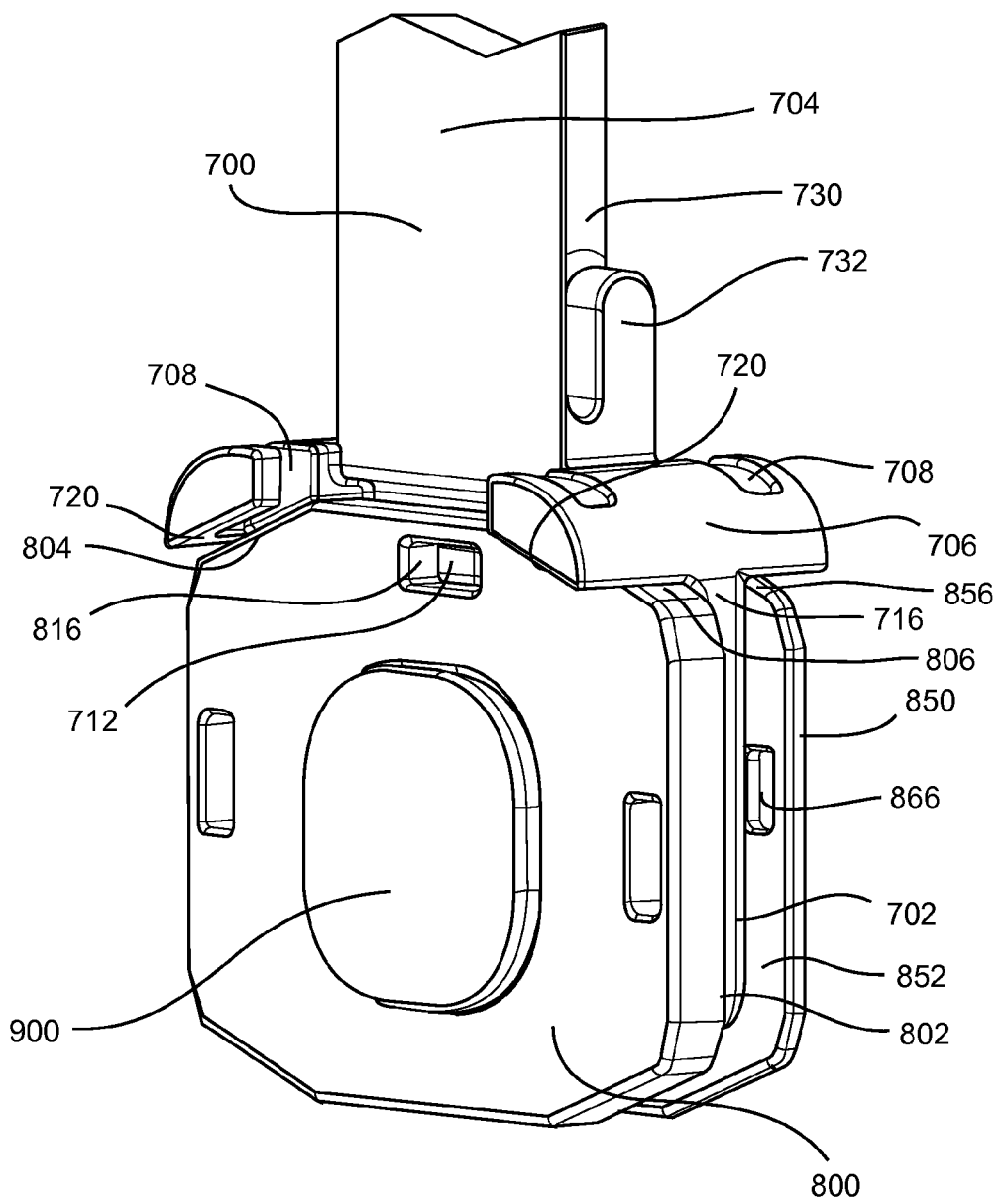
FIG. 18 is a perspective view of the distal end of the bearing holder shown in FIG. 17, attached to the superior bearing and the inferior bearing shown in FIG. 13.

FIG. 18 depicts a superior side view of superior bearing 800 and an inferior bearing 850 mounted on the bearing holder 700. In the embodiment depicted, the bearings 800, 850 are mounted in the anterior position; however they can also be mounted in either of the lateral positions, depending upon which surgical approach is used. Prior to mounting, the snap fasteners 900 are snapped onto the bearings 800, 850. The superior bearing 800 is mounted on the superior side 716 of the bearing holder 700. The superior bearing 800 is placed parallel to and adjacent to the body 710, with the cup 810 surrounded by the prongs 702. Anterior faceted edges 806 of the superior bearing 800 are flush against the slanted edges 720 of the shoulders 706. One tooth 728 of the locking key 712 protrudes into the anterior instrument port 816. Simultaneously, the inferior bearing 850 is placed on the inferior side 718 of the bearing holder 700, parallel to and adjacent to the body 710 and with the prongs 702 surrounding the dome 860. Anterior faceted edges 856 of the inferior bearing 850 are flush against the slanted edges 720 of the shoulders 706, and the other tooth 723 of the locking key 712 is protruding through the anterior instrument port 866. With both bearings 800, 850 held thus, the adjustment nut 726 is turned. The pin 722 and locking key 712 turn, and the teeth 728 on the locking key 712 engage and tighten down on the edges of the instrument ports 816, 866. The bearings 800, 850 are thus locked in place on the bearing holder 700. The inferior bearing surface 852 and the superior bearing surface 802 are adjacent to one another, with the dome 860 encircled by the cup 810 (not visible in FIG. 18).

Figure 19:
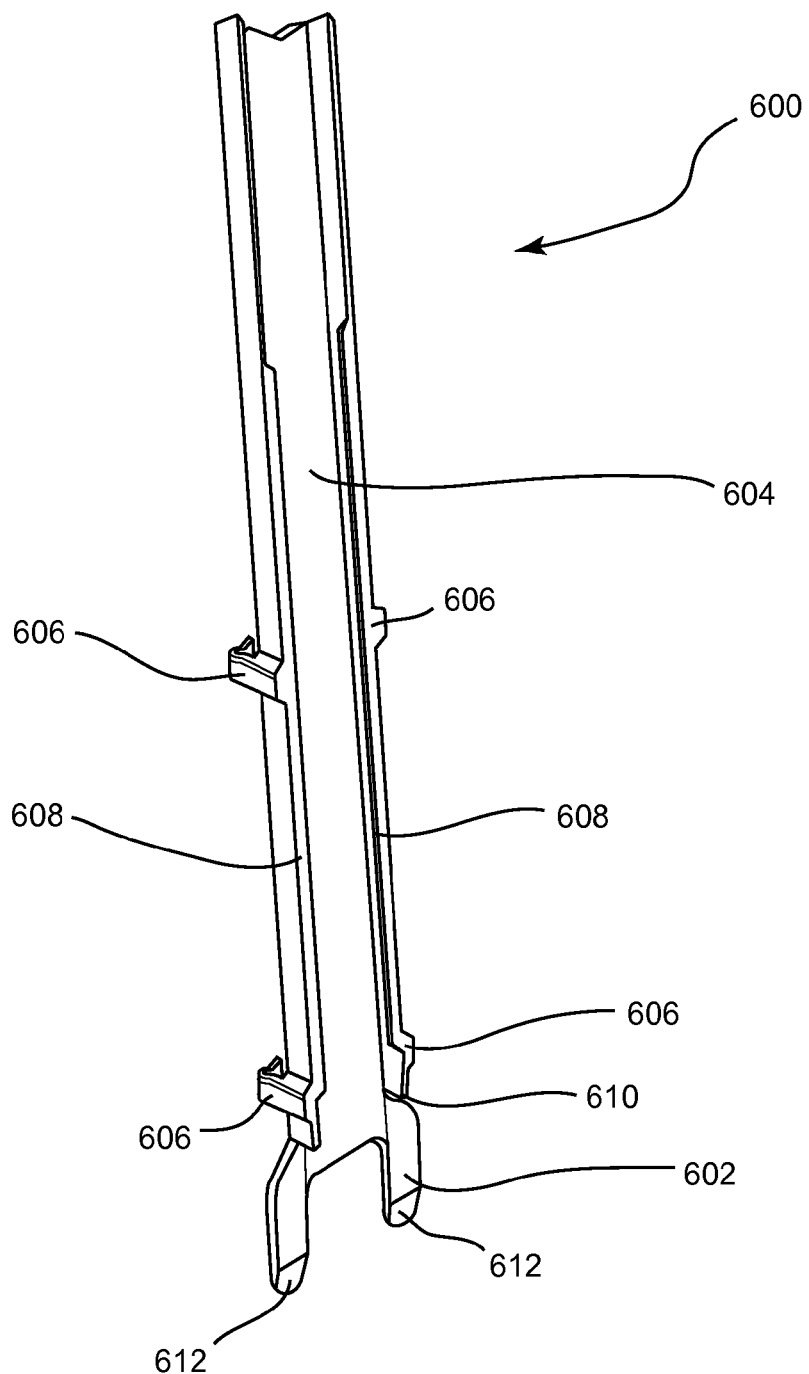
FIG. 19 is a perspective view of the distal end of a height compressor.

FIG. 19 illustrates the distal end of the height compressor 600. At the proximal end is a handle (not visible in FIG. 19). The height compressor 600 has a shaft 604 with two prongs 602 at its distal end 610. Each prong 602 terminates in an angled ramp 612. On either lateral side of the shaft 604 is a raised edge 608, which extends perpendicularly from the shaft 604 and bends to form an L-shape. Slightly above the distal end 610 of the shaft 604 is a pair of rails 606, with one rail 606 located on each raised edge 608. A second pair of rails 606 is located some distance proximally along the shaft 604, one on each raised edge 608.

Figure 20:
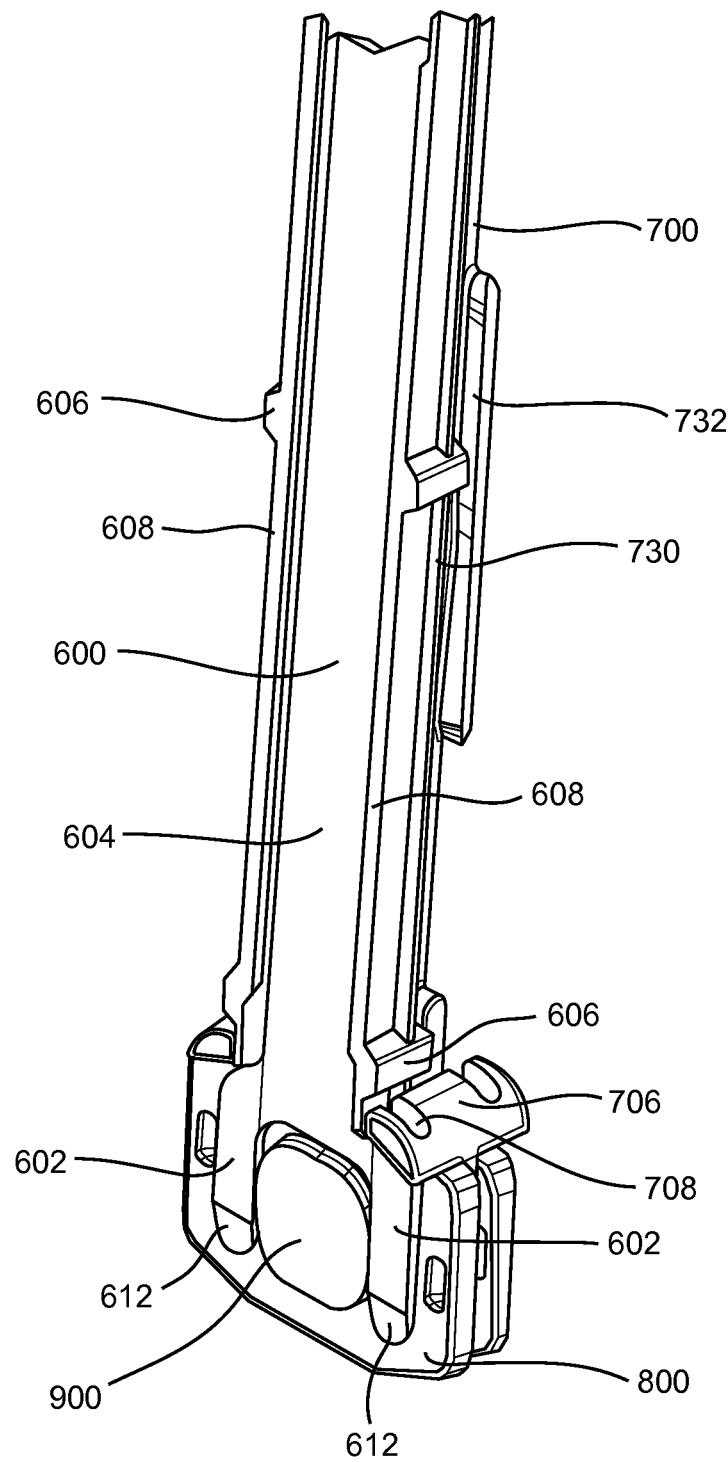
FIG. 20 is a perspective view of the distal end of the bearing holder and bearings shown in FIG. 18, attached to the height compressor shown in FIG. 19.
Figure 21:
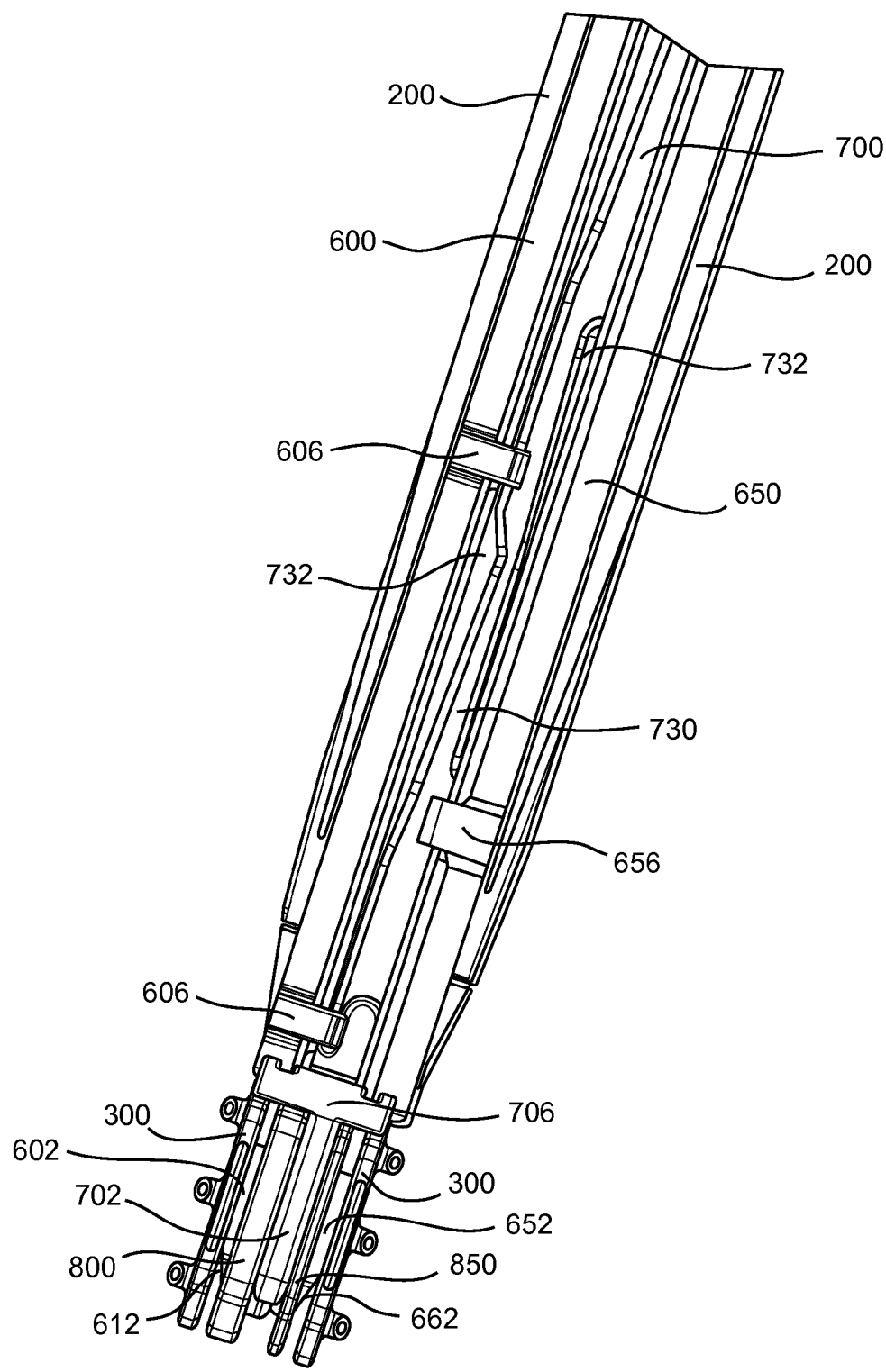
FIG. 21 is a side elevation view of the distal end of the bearing instrument assembly and implant shown in FIG. 3.

The bearing holder 700 with attached bearings 800, 850, and a height compressor 600 are shown in FIG. 20. The height compressor 600 is connected to the bearing holder 700 by sliding the height compressor 600 parallel to the bearing holder 700 in the distal direction, on the superior side 716, allowing the rails 606 to clasp the camming channel 730 on each side of the bearing holder 700. As the height compressor 600 slides, the prongs 602 slide into the slots 708 on the bearing holder 700. The height compressor 600 is slid distally until the rails 606 contact the shoulders 706 of the bearing holder 700. At this point the height compressor 600 cannot slide distally any farther and the prongs 602 encircle the snap fastener 900 on the superior bearing 800. The raised edges 608 are facing outward.

After the height compressor 600 is connected to the bearing holder 700, these two instruments and the attached bearings 800, 850 are inserted as a set between the end plate holders 200, as seen in FIG. 3. The angle compressor 650 is already in place, connected to one end plate holder 200, as seen in FIG. 16. The distal ends of the bearing holder 700 and the height compressor 600, with the attached bearings 800, 850 are inserted between the end plate holders 200, oriented so that the height compressor 600 is slid in next to the end plate holder 200 which is suspended from the height adjustment arm 156 (seen in FIG. 6).The height compressor 600, bearing holder 700 and bearings 800, 850 are slid in a distal direction parallel to the end plate holders 200. As the instruments are slid in, the rails 656 of the angle compressor 650 slide into the camming channels 730 on the bearing holder 700, and the prongs 652 slide into the slots 708. Simultaneously, the raised edges 608 of the height compressor 600 clasp the lateral grooves 212 of the end plate holder 200. The instrument set is slid distally until the shoulders 706 of the bearing holder 700 contact the end plates 300. At this point, the instrument set cannot slide in any farther and the prongs 652 of the angle compressor 650 encircle the snap fastener 900 between the end plate 300 and the inferior bearing 850.

All components of the intervertebral disc motion preservation implant 14 are now in position between the vertebral bodies. FIG. 211 illustrates the implant 14 held in place by the end plate holders 200 and bearing holder 700. To attach the bearings 800, 850 to the end plates 200 the height and angle compressors 600, 650 are removed, one at a time, in either order. The height compressor 600 is removed by grasping the handle and pulling it proximally. As the height compressor 600 slides out, the rails 606 slide proximally along the camming channels 730 of the bearing holder 700. As the height compressor 600 is removed, the prongs 602 are slid out from between the end plate 300 and the superior bearing 800. Just when the prongs 602 reach the point where they are no longer between the end plate 300 and the superior bearing 800, the rails 606 slide over a widening in the undulating edges 732 of the camming channels 730. This forces the bearing holder 700 slightly closer to compressor 600, and therefore closer to the end plate holder 200. Since the prongs 602 of the height compressor 600 are no longer between the end plate 200 and the superior bearing 800, the additional force snaps the snap fastener 900 on the bearing 800 into place in the snap port 330 on the end plate 200.

The angle compressor 650 is removed in the same way. The angle compressor 650 is removed by grasping the handle and pulling it proximally. As the angle compressor 650 slides out, the rails 656 slide proximally along the camming channels 730 of the bearing holder 700. As the angle compressor 650 is removed, the prongs 652 are slid out from between the end plate 300 and the inferior bearing 850. Just when the prongs 652 reach the point where they are no longer between the end plate 300 and the inferior bearing 850, the rails 656 slide over a widening in the undulating edges 732 of the camming channels 730. This forces the bearing holder 700 slightly closer to compressor 650, and therefore closer to the end plate holder 200. Since the prongs 652 of the angle compressor 650 are no longer between the end plate 200 and the inferior bearing 850, the additional force snaps the snap fastener 900 on the bearing 850 into place in the snap port 330 on the end plate 200. The adjustment null. 726 on the bearing holder 700 is turned, so the teeth 728 disengage from the instrument ports 816, 866. All components of the intervertebral implant 14 are now in place between the end plates 200.

Referring to FIGS. 3 and 8, the bearing holder 700 is removed by grasping its handles 734 and pulling it proximally between the end plate holders 200 until it is free of the end plate holders 200 and the pivot assembly 18. Each end plate holder 200 is disengaged from its end plate 300 by raising the lever 222. Raising the lever 222 retracts the spreader 220, and the prongs 202 are loosened within the pocket 310. The end plate holder 200 can now be removed by pulling it proximally away from the end plate 200. Thus all of the instrument assembly 17 is removed from the patient.

Should removal of the implant 14 or replacement of any of its constituent components be required, such procedure may be carried out in any of the three approaches; anterior, right lateral, or left lateral, regardless of which approach was used during the initial implantation. To remove any component, first each end plate holder 200 is connected to the pivot assembly 18, as seen in FIG. 6, with the lever 222 in the lowered position. The prongs 202 are guided into the pocket 310 of the end plate 300, and the lever 222 is raised. The spreader 220 moves distally, and the prongs 202 are spread into the pocket corners 312. With the end plate holders 200 now connected to the end plates 300, the bearing holder 700 is inserted between the end plate holders 200, The bearing holder 700 is oriented so that the superior side 716 is facing the end plate holder 200 which is connected to the height adjustment guide arm 156, and the inferior side 718 is facing the end plate holder 200 which is connected to the angle adjustment guide arm 116. As the bearing holder 700 is inserted, the prongs 702 will slide between the bearings 800, 850 such that the prongs 702 lie on either side of the dome 860. When the prongs 702 are in place, the adjustment nut 726 is turned, so that the teeth 728 engage in the instrument ports 816, 866, and the bearings 800, 850 are locked to the bearing holder 700.

Next, the compressors 600, 650 are inserted in either order. The height compressor 600 is slid distally along the end plate holder 200 which is connected to the height adjustment guide arm 156, so that the raised edges 608 slide into and along the lateral groove 212. As the compressor is slid distally along the end plate holder, the rails 606 slide over the undulating edges 732 and into the camming channel 730. When the ramps 612 on the prongs 602 slide in between the end plate 300 and the superior bearing 800, their intrusion will pry the snap fastener 900 apart from the snap port 330. The angle compressor 650 is then slid distally along the end plate holder 200 which is connected to the angle adjustment guide arm 116, so that the raised edges 658 slide into and along the lateral groove 212, and the rails 656 slide along the camming channel 730. When the ramps 662 on the prongs 652 slide in between the end plate 300 and the inferior bearing 850, their intrusion will pry the snap fastener 900 apart from the snap port 330.

The bearings 800, 850 are now free from the end plates 300, and attached to the bearing holder 700. The bearing holder 700 with the attached hearings 800, 850, and the compressors 600, 650 are removed simultaneously, by grasping their handles and pulling them proximally out from between the end plate holders 200. At this juncture new bearings 800, 850 may be inserted in the same manner as described previously.

An alternative embodiment of the invention is illustrated in FIGS. 22-33. This embodiment uses many of the same instruments as described for the previous embodiment, and is configured to implant the implant 14, a fusion block, or an alternative implant. The alternative embodiment comprises alternative bearing placement guidance instrumentation, and compression instrumentation.

Figure 22:
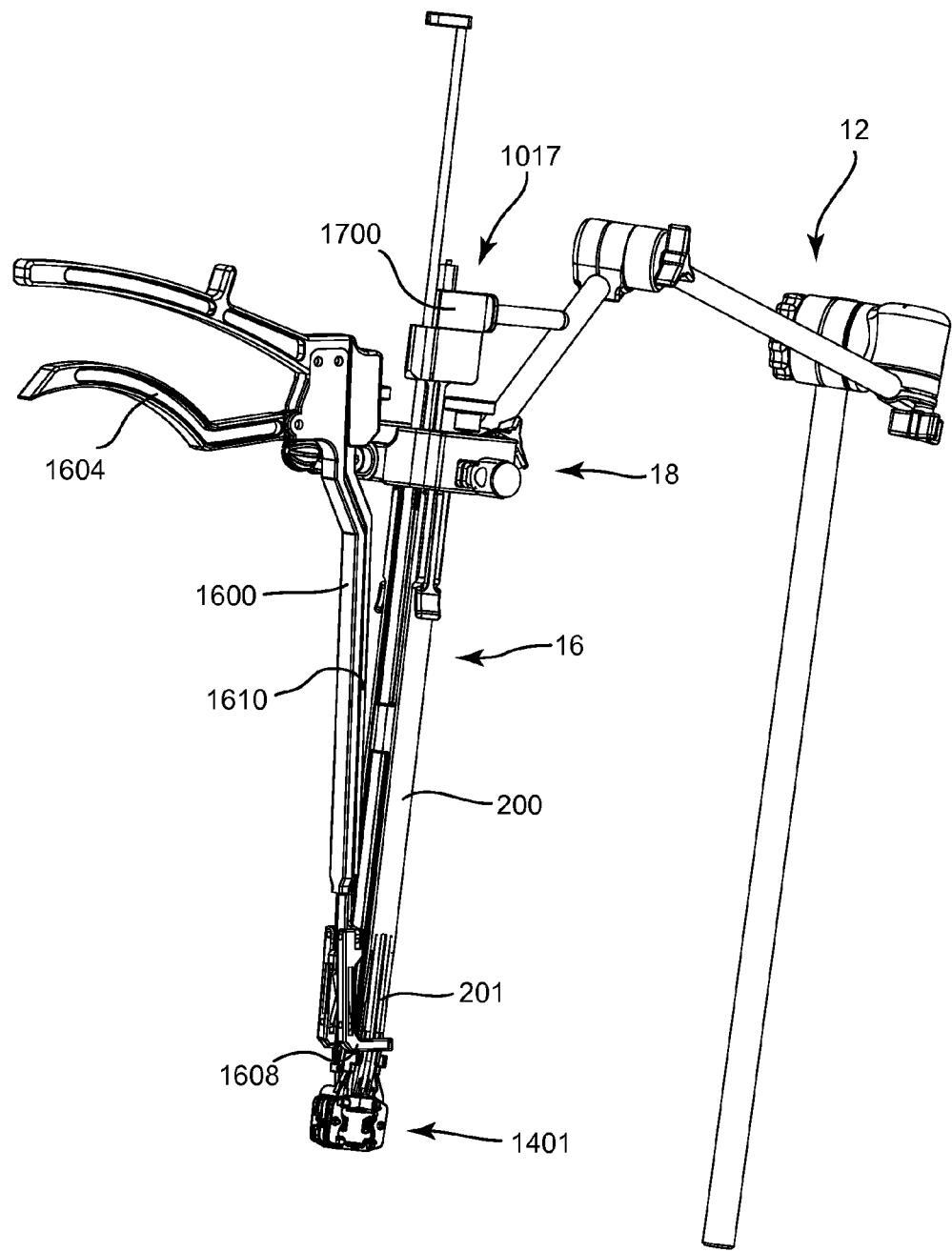
FIG. 22 is a perspective view of an alternative bearing guidance assembly, the support assembly, the pivot assembly and the end plate assembly.

Referring to FIG. 22, the support assembly 12, pivot assembly 18 and end plate assembly 16 are shown with an alternative bearing guidance assembly 1017, an alternative implant 1014, and a compressor 1600. The bearing guidance assembly 1017 comprises a bearing holder 1700 with guidance features. The implant 1014 comprises two end plates 1300, a superior bearing 1800, an inferior bearing 1850, and two snap fasteners 1900. The bearing holder 1700 holds and guides the superior and inferior bearings 1800, 1850 as they are inserted between the end plates 1300. The compressor 1600 provides compressive force to the end plates 1300, pushing them toward the bearings 1800, 1850 causing the snap fasteners 1900 to engage to the end plates 1300, thus connecting the end plates 1300 to the bearings 1800, 1850. The compression instrumentation also includes feeler gauges (not shown in FIG. 22) which test the snap fastener connection. Although the alternative implant 1014 is depicted in FIGS. 22-28, the alternative bearing guidance assembly 1017 could also be used to place the implant 14, or a fusion block.

Figure 23:
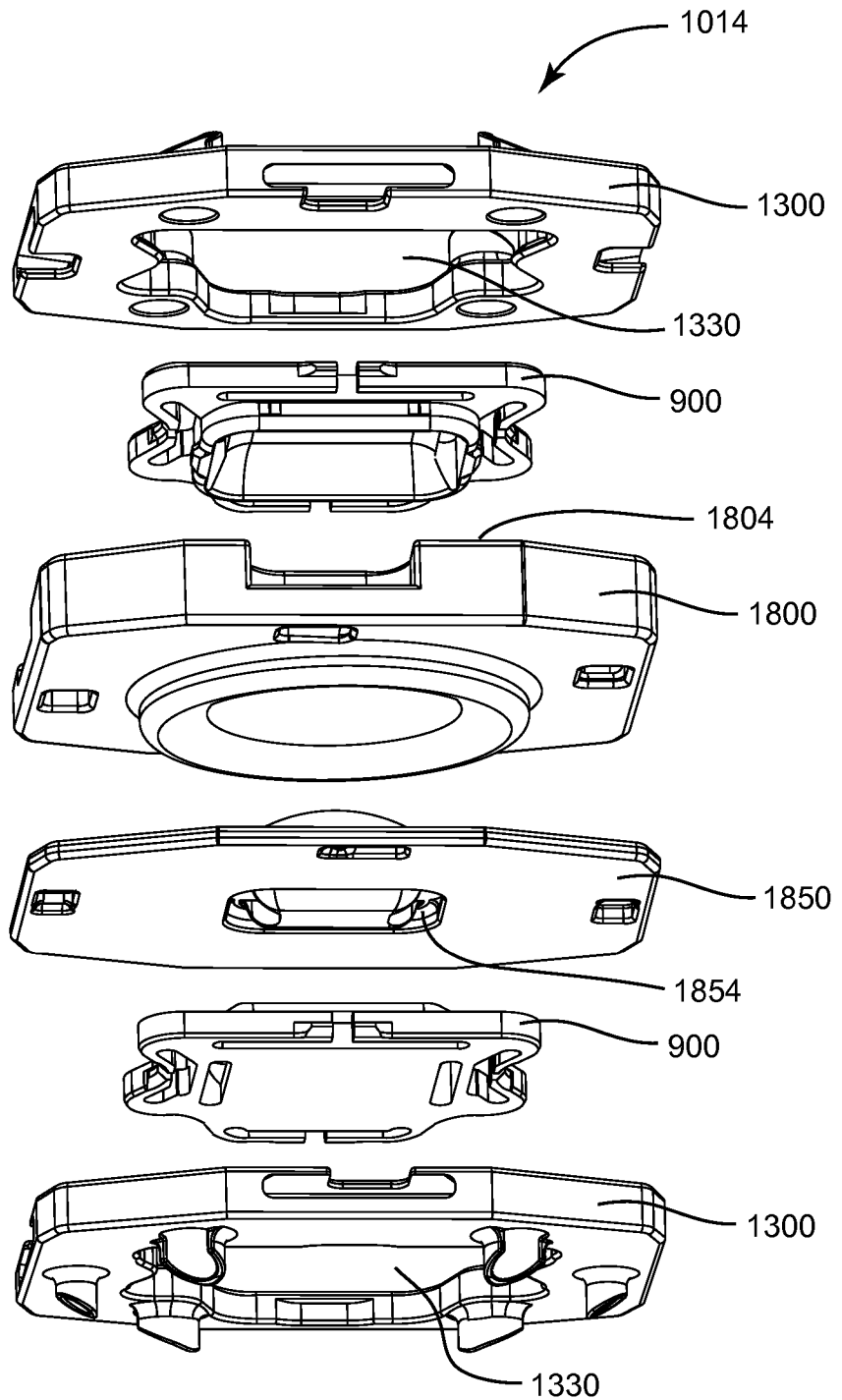
FIG. 23 is an enlarged exploded view an alternative disc motion preservation implant.

Referring to FIG. 23, an enlarged exploded view of the alternative disc motion preservation implant 1014 is depicted. Each end plate 1300 has a snap port 1330. The superior bearing 1800 has a trough 1804 on its superior side, and the inferior bearing 1850 has a trough 1854 on its inferior side. The snap fasteners 1900 connect the end plates to the superior and inferior bearings when all components of the implant are snapped together. Prior to implantation, one snap fastener 1900 is snapped into the trough 1804 on the superior bearing 1800, and similarly the second snap fastener 1900 is snapped into the trough 1854 on the inferior bearing 1850.

Figure 24:
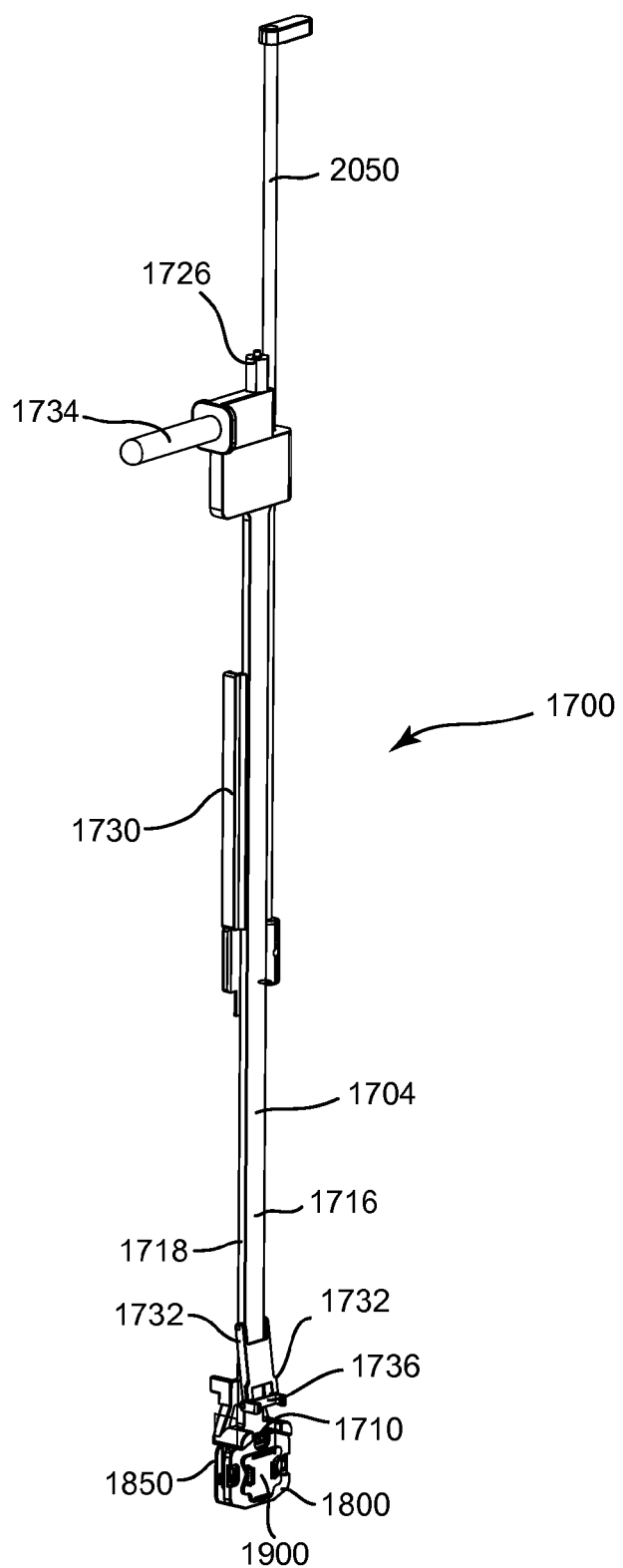
FIG. 24 is a perspective view of a bearing holder, holding the bearing components of the implant of FIG. 23.

FIG. 24 depicts the bearing holder 1700, holding the superior and inferior bearings 1800, 1850. A snap fitting 1900 is attached to each bearing 1800, 1850. The superior bearing 1800 is held on a superior side 1716 of the bearing holder 1700, and the inferior bearing 1850 is held on an inferior side 1718. The bearing holder 1700 has two handles 1734 at the proximal end, and a shaft 1704 which terminates at its distal end at an intersection with a body 1710. Along a portion of each lateral side of the shaft 1704 is guide rail 1730, which extend perpendicularly from the shaft 1704 on the inferior side 1718. Near the distal end of the shaft 1704, a pair of slider arms 1732 extends from the superior side 1716, holding a slider link 1736. An inferior feeler gauge 2050 is slidably engaged on the shaft 1704 of the bearing holder 1700.

Figure 25:
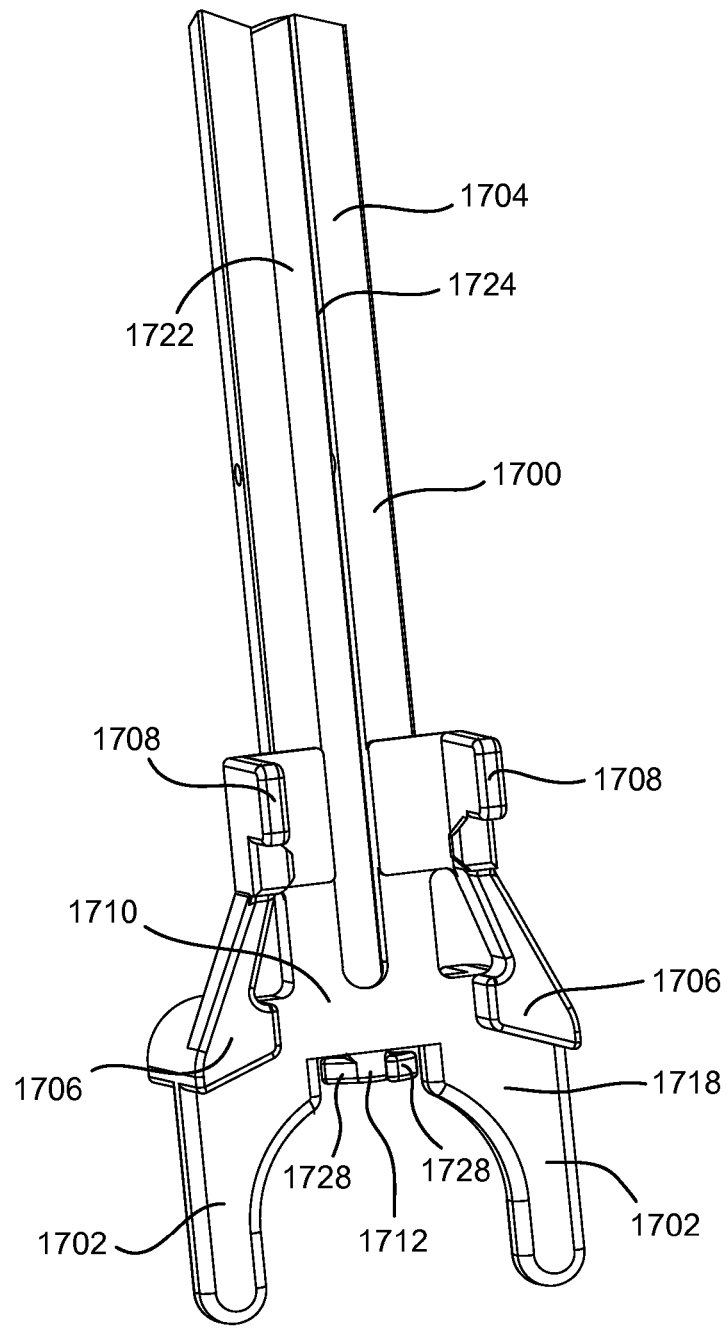
FIG. 25 is an enlarged view of an inferior side of a distal end of the bearing holder of FIG. 24.

Referring to FIG. 25, an enlarged view of the inferior side 1718 of distal end of the bearing holder 1700 is shown. At the end of the shaft 1704, the body 1710 extends distally and splits into two prongs 1702. The body 1710 and prongs 1702 are generally flat and fork-like in shape. Where the body 1710 originates at the base of the shaft 1704 are two stops 1708, one on each lateral side of the shaft 1704, which protrude perpendicularly from the shaft on the inferior side 1718. Distal from the stops 1708, where the two prongs 1702 extend from the body 1710, are two shoulders 1706, one on each lateral side of the body 1710. Each shoulder 1706 extends perpendicularly from the body 1710 in both superior 1716 and inferior 1718 directions.

Where the two prongs 1702 meet at the base of the body 1710 is a locking key 1712 with two teeth 1728. The locking key 1712 is mounted on the end of a pin 1722 that extends from the proximal end of the shaft to the distal end, and is enclosed in a channel 1724. At the proximal end of the bearing holder 1700, the pin 1722 emerges from the channel 1724 and is capped by an adjustment nut 1726 (seen in FIG. 23). When the adjustment nut 1726 is turned, the pin 1722 and the locking key 1712 turn.

Figure 26:
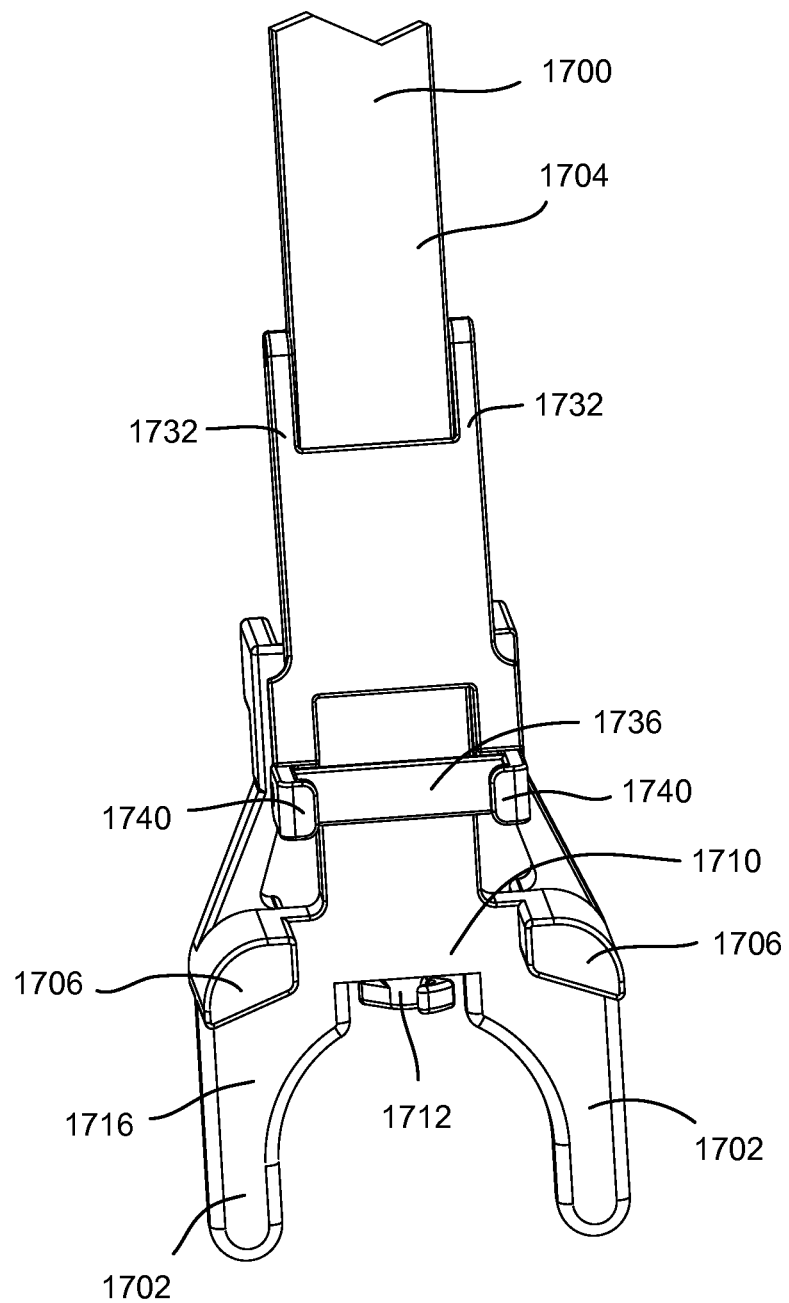
FIG. 26 is an enlarged view of a superior side of the distal end of the bearing holder of FIG. 24.

Referring to FIG. 26, an enlarged view of the superior side 1716 of the distal end of the bearing holder is shown. Just proximal to the body 1710, a slider arm 1732 is linked to each side of the shaft 1704. Extending between the ends of the arms 1732 is the slider link 1736, which has a guide rail 1740 at each of its lateral ends. The guide rails 1740 are configured to grip the lateral edges of the end plate holders 1200 as the bearings 1800, 1850 are inserted or withdrawn, thus guiding the bearings in between the end plates 1300.

Figure 27:
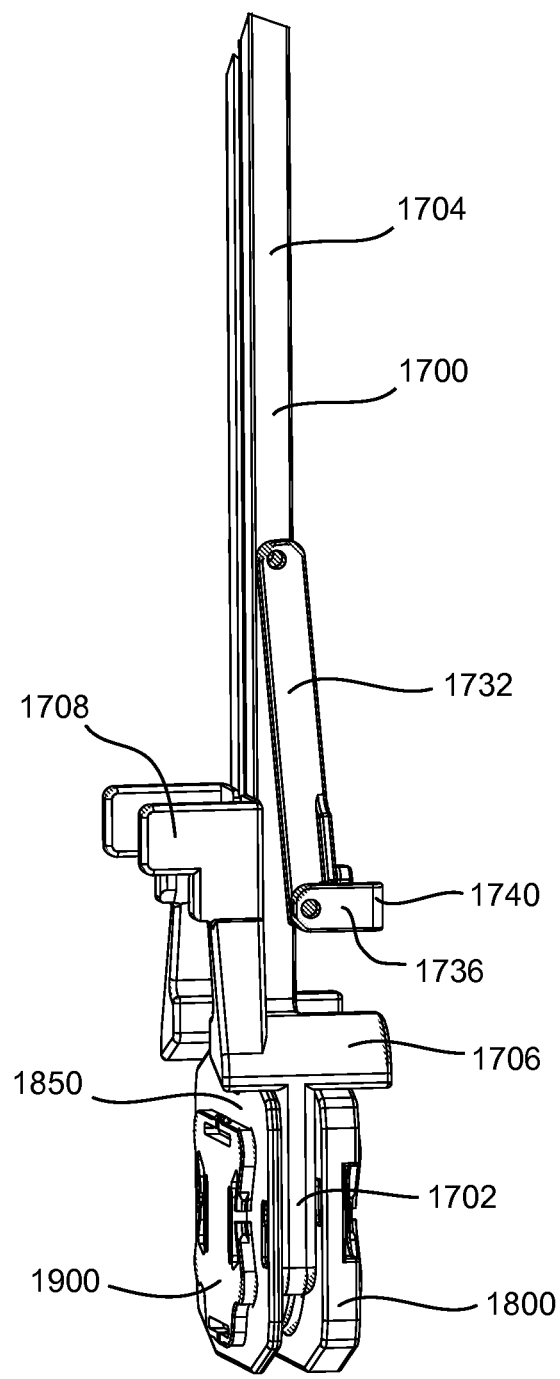
FIG. 27 is an enlarged view of a superior and an inferior bearing mounted on the distal end of the bearing holder.

Referring to FIG. 27, an enlarged view shows the bearings 1800, 1850 mounted on the distal end of the bearing holder 1700. The bearings 1800, 1850 are mounted on the bearing holder 1700 in the same manner as described previously for the bearings 800, 850 and the bearing holder 700.

Figure 28:
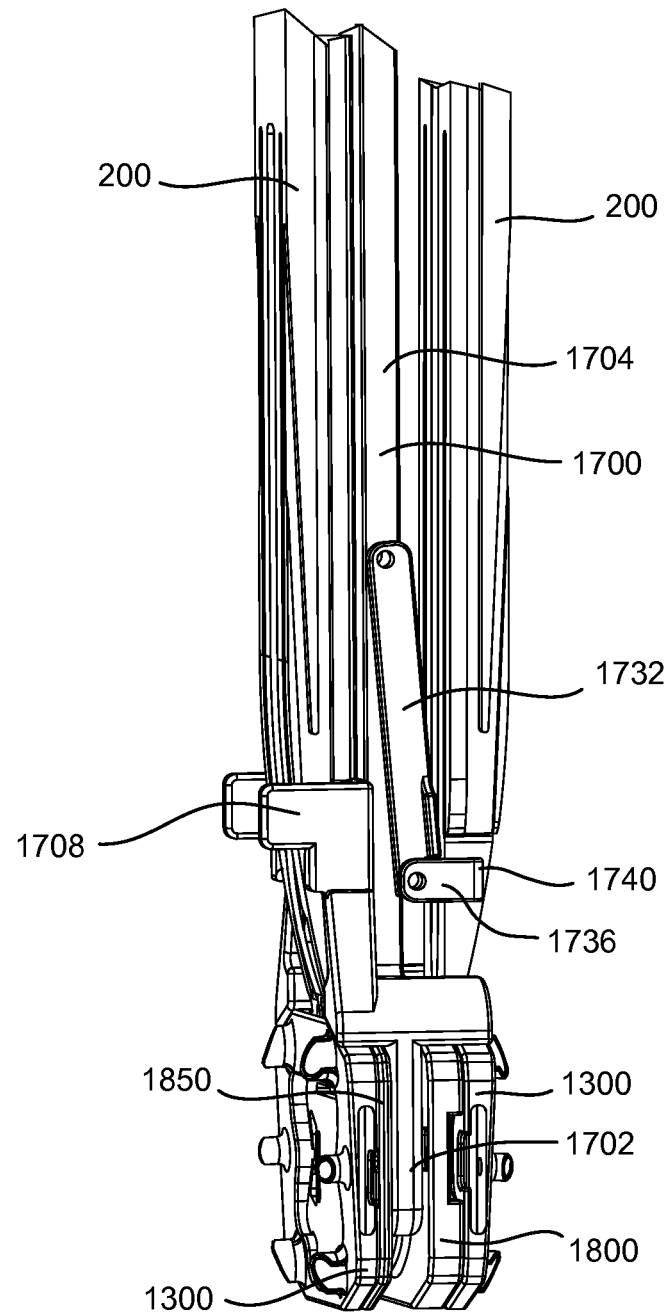
FIG. 28 is an enlarged view of the bearing holder with mounted bearings inserted in the end plate assembly.

Referring to FIG. 28, the bearing holder 1700 with mounted bearings 1800, 1850 is shown inserted between the end plate holders 200 and the end plates 1300. The bearing holder 1700 and bearings 1800, 1850 are slid in between the proximal ends of end plate holders 200 as they are held in the pivot assembly 18. As the bearing holder 1700 is slid distally, the guide rails 1730 are maneuvered so that they clasp the edges of the inferior end plate holder 200. Similarly, the guide rails 1740 clasp the edges of the superior end plate holder 200. With the guide rails 1730, 1740 thus engaged, the bearings 1800, 1850 are able to slide in between the end plates 1200 with a minimum of lateral movement and adjustment. When the bearings 1800, 1850 reach the end plates 1200, the shoulders 1706 of the bearing holder 1700 contact the end plates 1300, preventing any further distal movement, and lining the bearings 1800, 1850 up so that the snap fasteners 1900 will correctly engage with the end plates 1300 when compressed.

Figure 29:
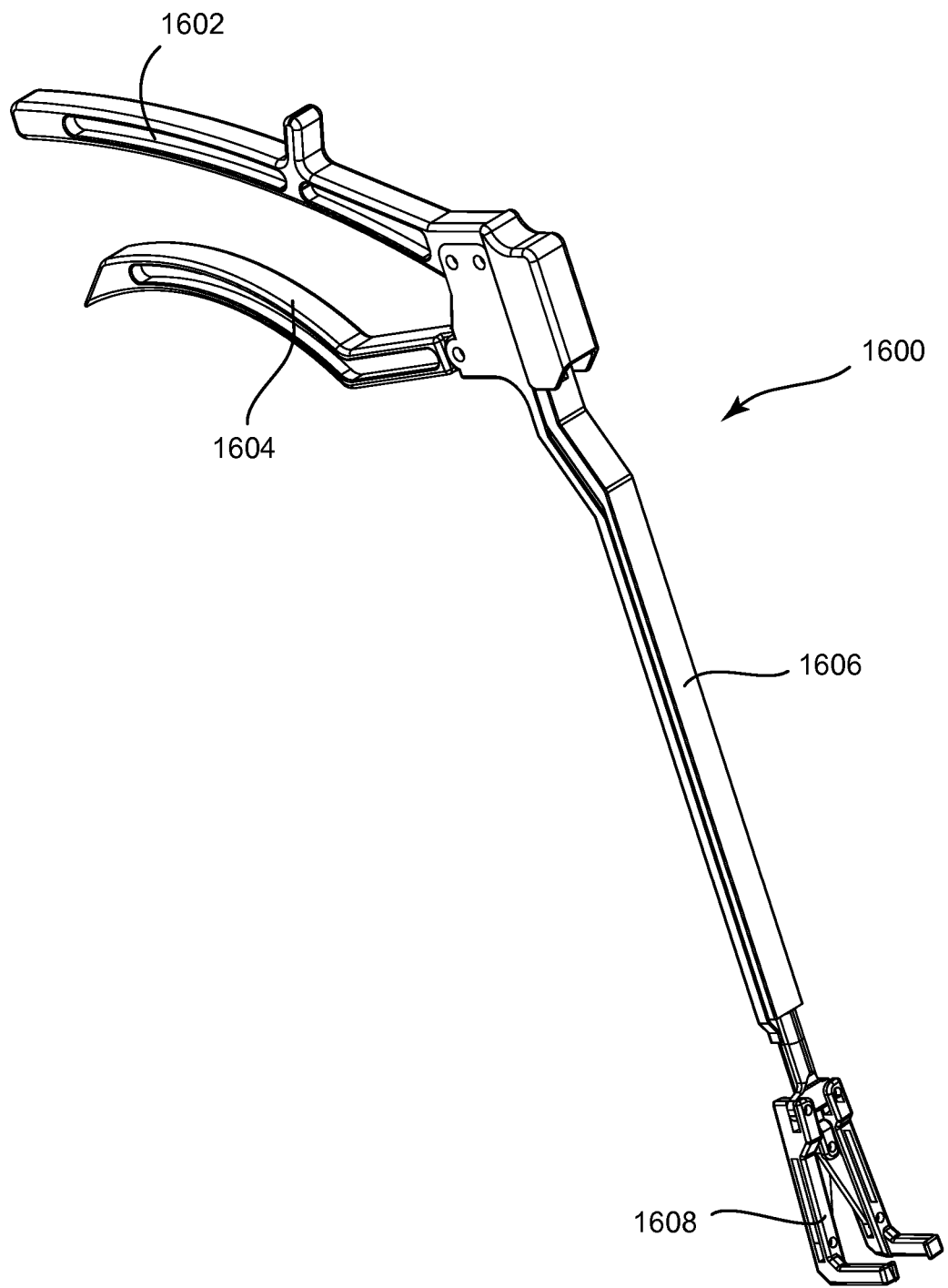
FIG. 29 is a perspective view of a compressor.

Referring to FIG. 29, a compressor 1600 is shown. The compressor 1600 has a handle 1602, a compression lever 1604, a shaft 1606 and at the distal end of the shaft 1606, a pair of tongs 1608. When the compressor 1600 is implemented, the tongs 1608 push the end plates 1300 toward the bearings 1800, 1850, providing force so the snap fasteners 1900 snap into the snap ports 1330 on the end plates 1300.

Figure 30:
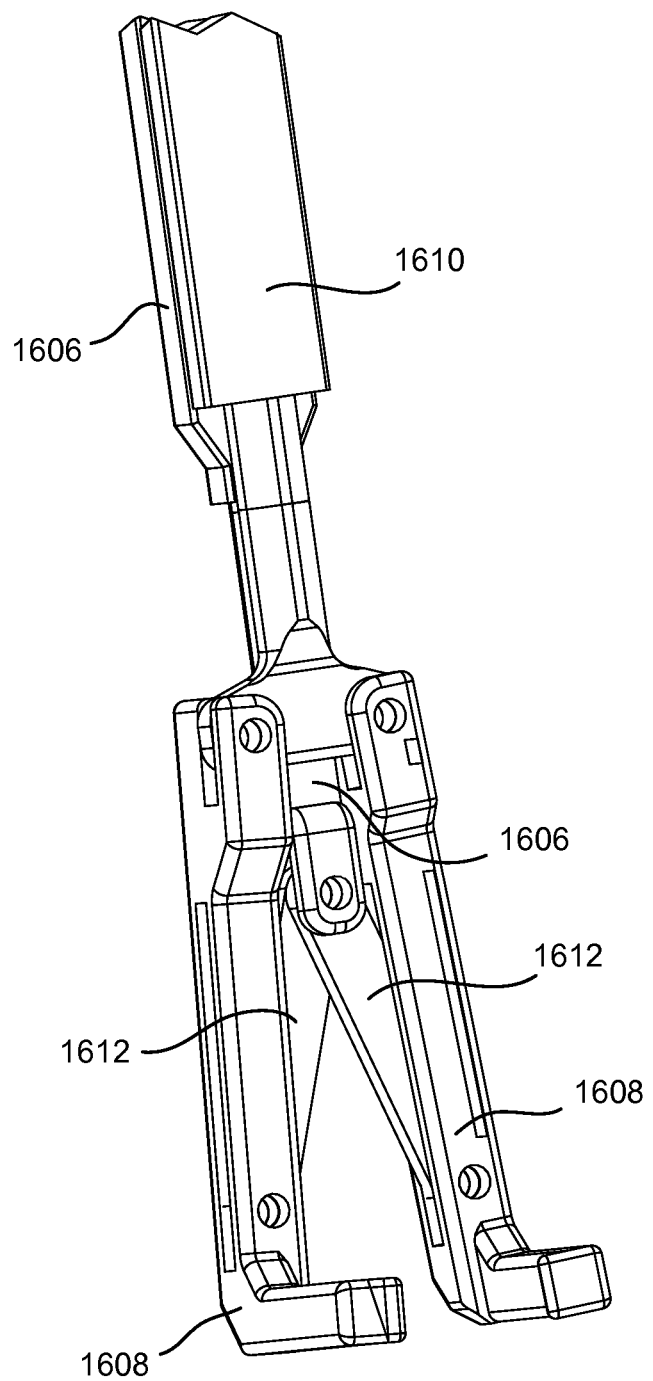
FIG. 30 is an enlarged view of the distal end of the compressor of FIG. 29.

Referring to FIG. 30, an enlarged view of the distal end of the compressor 1600 is shown. Extending lengthwise along the shaft 1606 is a pull bar 1610, which is pivotably connected at its proximal end to the compression lever 1604, and is pivotably connected at its distal end to the tongs 1608. The tongs 1608 are pivotably connected to a pair of cross links 1612, which are pivotably connected to the distal end of the shaft 1606. When the compression lever 1604 is pulled toward the handle 1602, the pull bar 1610 moves distally parallel to the shaft 1606, and the tongs 1608 are forced together.

Returning to FIG. 22, the end plate assembly 16 and the bearing guidance assembly 1017 are shown, with the compressor 1600 grasping the end plate holders 200. The compressor 1600 is placed so that each tong 1608 is adjacent to the shaft 201 of each end plate holder 200. The compression lever 1604 is raised, thus extending the pull bar 1610 and pulling the tongs 1608 together, which push the end plate holders 200 with the attached end plates 1300 together. The snap fasteners 1900, which are already engaged in the troughs on the bearings 1800, 1850, are pushed into the snap ports 1330 on the end plates 1300.

Figure 31:
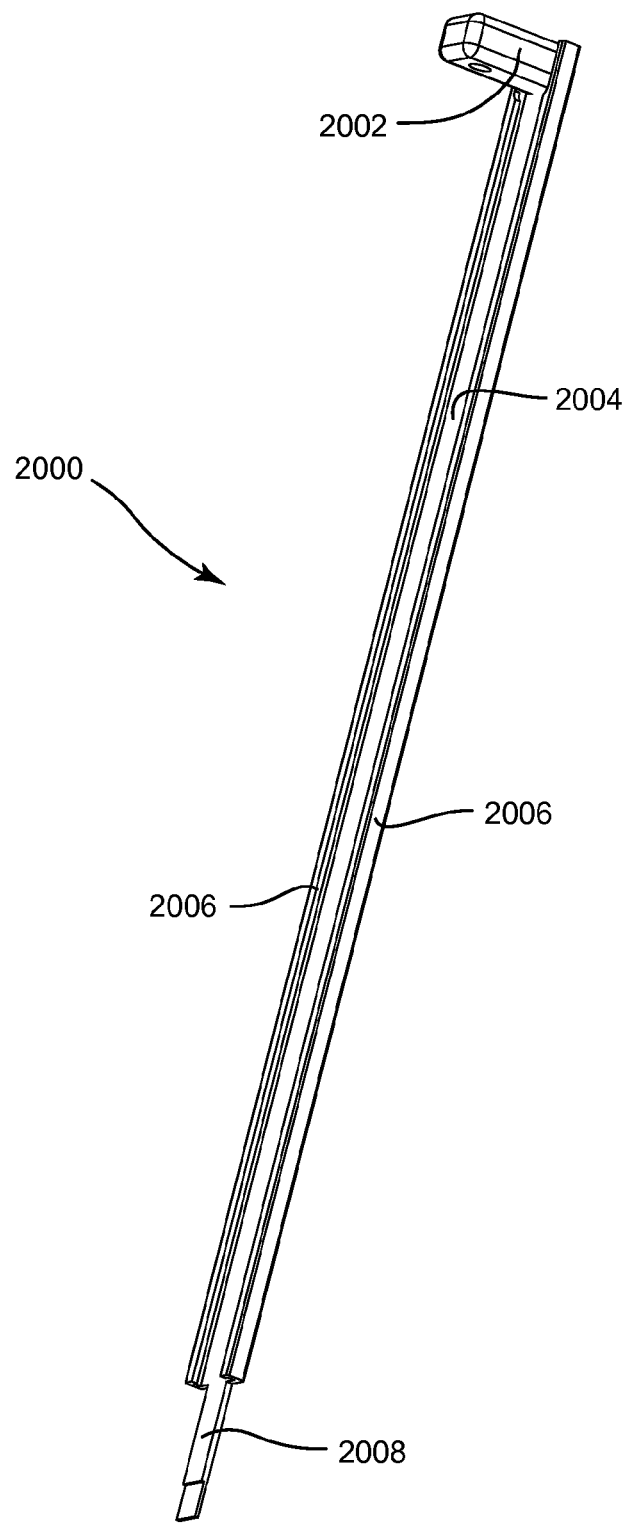
FIG. 31 is a perspective view of a superior feeler gauge.

Referring to FIG. 31, a superior feeler gauge 2000 is shown. The superior feeler gauge 2000 has a handle 2002 and a wide shaft 2004 with guide rails 2006 on each lateral side of the shaft 2004. The shaft 2004 terminates at a tang 2008 which extends distally from the distal end of the shaft 2004.

Figure 32:
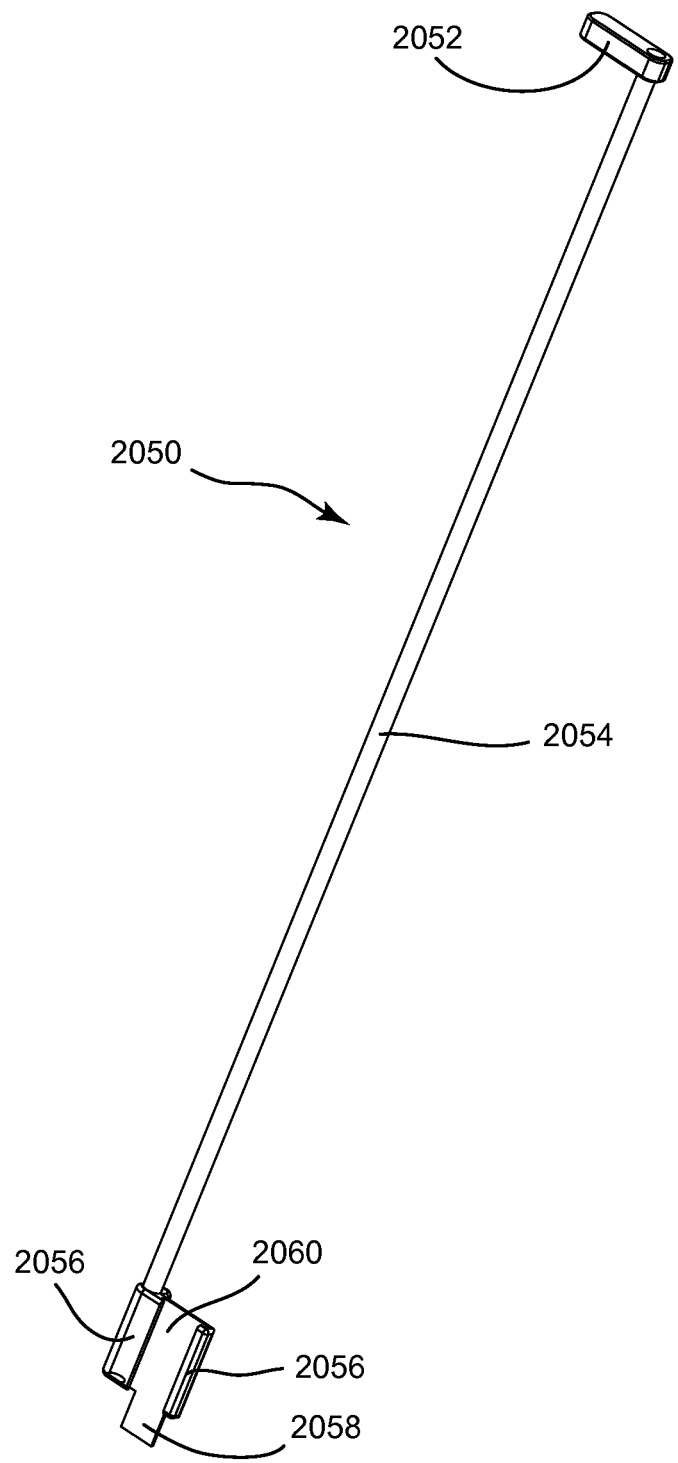
FIG. 32 is a perspective view of an inferior feeler gauge.

Referring to FIG. 32, the inferior feeler gauge 2050 is shown. The inferior feeler gauge 2050 has a handle 2052, a shaft 2054, and a body 2060. Guide rails 2056 line each lateral edge of the body 2060, and they enable the gauge 2050 to be slidably engaged to the bearing holder 1700. At the distal end of the body 2060, a tang 2058 extends distally from the body 2060.

The feeler gauges 2000, 2050 are used to test if the snap fasteners 1900 have properly snapped to the end plates 1300 following compression. The compressor 1600 is removed from the instrument assembly 1017, and the superior feeler gauge 2000 is inserted between the end plate holders 200 and the bearing holder 1700. The inferior feeler gauge 2050 is already engaged on the bearing holder 1700, as seen in FIG. 24. The superior feeler gauge 2000 is inserted on the superior side 1716 of the bearing holder 1700, so that its guide rails 2006 clasp the edges of the superior bearing holder 200. The gauge 2000 is slid distally until its tang 2008 slides in between the superior end plate 1300 and the superior bearing 1800. If the snap connection between the end plate 1300 and the bearing 1800 has been successfully made, the tang 2008 will not be able to slide between the snap fastener 1900 and the end plate 1300. If, however, the snap fastener 1900 has failed to engage with the snap port 1330 on the end plate 1300, the tang 2008 will continue to slide distally until it lies between the snap fastener 1900 and the end plate 1300.

Similarly, the inferior feeler gauge 2050 is slid distally until its tang 2058 slides in between the inferior end plate 1300 and the inferior bearing 1850. If the snap connection between the end plate 1300 and the bearing 1850 has been successfully made, the tang 2058 will not be able to slide between the snap fastener 1900 and the end plate 1300. If, however, the snap fastener 1900 has failed to engage with the snap port 1330 on the end plate 1300, the tang 2058 will continue to slide distally until it lies between the snap fastener 1900 and the end plate 1300.

If either snap fastener 1900 has failed to engage with its corresponding end plate 1300, the feeler gauges 2000, 2050 are slid proximally, and the compressor 1600 is realigned with the end plate holders 200. Compression is again attempted, and re-tested with the feeler gauges until both snap fasteners 1900 are snapped in place on the end plates 1300.

Figure 33:
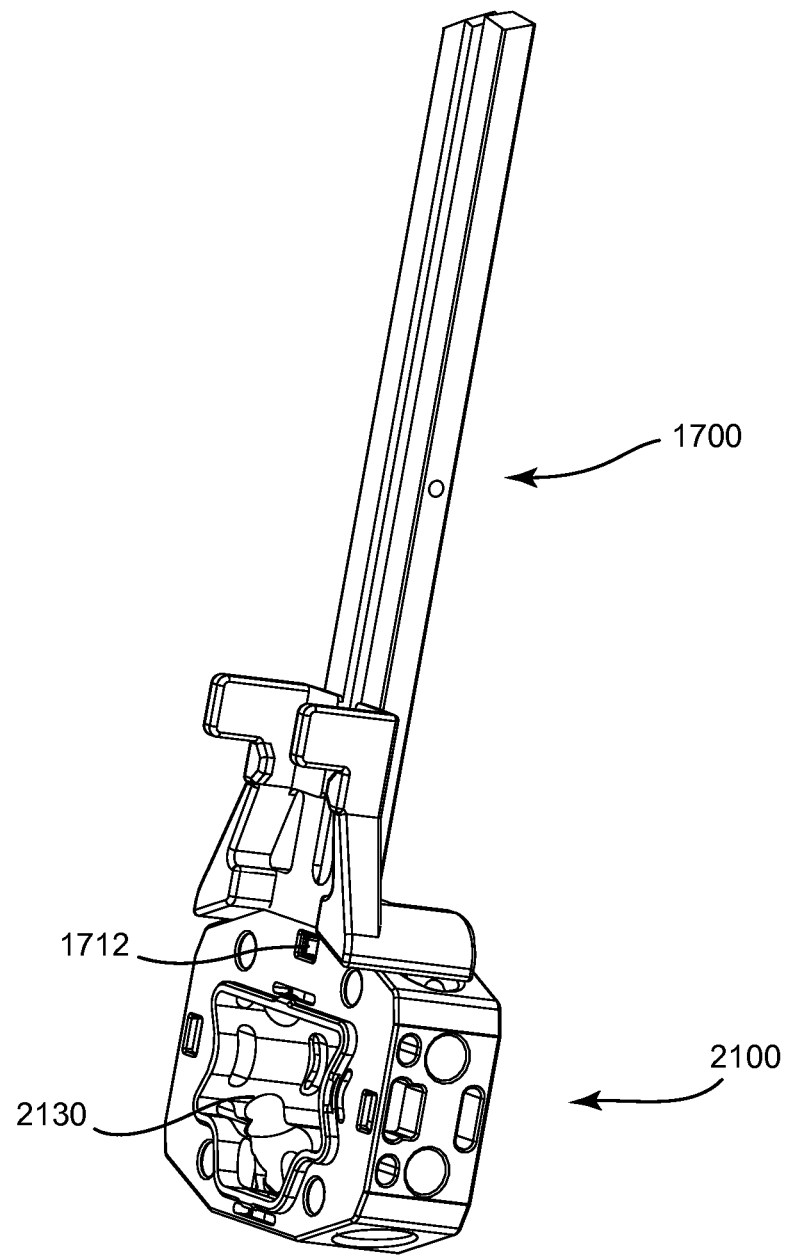
FIG. 33 is a perspective view of a fusion block attached to the distal end of the bearing holder of FIG. 24.

Referring to FIG. 33, a fusion block 2100 is shown attached to the distal end of the bearing holder 1700. When fusion instead of motion preservation is desired, the fusion block 2100 may be inserted in between two end plates 1300 in the intervertebral space, using the same bearing delivery methods as described previously. The fusion block 2100, with two snap fasteners 1900 snapped onto each of its two snap ports 2130, is locked on the end of the bearing holder 1700 using the locking key 1712 mechanism. The fusion block 2100 and snap fasteners 1900 are inserted between the end plates 1300, and snapped to the end plates 1300 using the compressor 1600.

It is appreciated that the bearing set 1800, 1850 and the fusion block 2100 are interchangeable, using the same instrumentation and implantation methods. If a motion preservation implant has been implanted, but a change to fusion is desired, the patient may be reopened, and the original implant removed with the instrumentation described above. A fusion block may then be implanted with the same instrumentation. If fusion is to be replaced with a motion preservation implant, the procedure may be reversed. It is also appreciated that all procedures described above may be carried out from an anterior approach, a right lateral approach, or a left lateral approach. Scar tissue buildup may be reduced by carrying out any revisions by a different approach, e.g., original implantation from an anterior approach and revision from a left or right lateral approach, or vice versa.

The present invention may be embodied in other specific forms without departing from its spirit or essential characteristics. It is appreciated that various features of the above-described examples can be mixed and matched to form a variety of other alternatives. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An intervertebral implant delivery system comprising:
a first end plate holder comprising a first end and a second end;
a second end plate holder comprising a first end and a second end; and
a pivot assembly that couples the first and second end plate holders together;
wherein each of the first ends independently retains an end plate of an intervertebral implant to facilitate insertion of the end plate into an intervertebral space;
wherein the pivot assembly is configured to actuate the second ends while the first ends are in the intervertebral space to adjust a thickness of a space between the end plates and adjust an angulation of the first end plate relative to the second end plate.

2. The intervertebral implant delivery system of claim 1, wherein the angulation comprises an anterior-posterior angulation, wherein the end plate holder is adjustable interoperatively from a lateral approach to determine the angulation.

3. The intervertebral implant delivery system of claim 1, wherein at least one of the first end plate holder, the second end plate holder, and the pivot assembly comprises a support feature attachable to a stationary frame to keep the pivot assembly substantially stationary.

4. The intervertebral implant delivery system of claim 3, further comprising the stationary frame, wherein the support feature comprises a ball extending from the pivot assembly to permit polyaxial positioning of the pivot assembly relative to the stationary frame.

5. The intervertebral implant delivery system of claim 1, further comprising a spike guard shaped to protect a first vertebral body adjacent to the intervertebral space from contact with at least one spike extending from the intervertebral implant.

6. The intervertebral implant delivery system of claim 1, further comprising a first spacer insertable between the first and second end plate holders to urge the end plates toward first and second vertebral bodies, respectively, wherein the first and second vertebral bodies bound the intervertebral space.

7. The intervertebral implant delivery system of claim 6, further comprising a second spacer insertable between the first and second end plate holders to further urge the end plates toward the first and second vertebral bodies.

8. The intervertebral implant delivery system of claim 1, further comprising an intermediate component holder configured to hold a first intermediate component and to facilitate insertion of the first intermediate component into the space between the end plates.

9. The intervertebral implant delivery system of claim 8, wherein the first intermediate component comprises a first articulating bearing, wherein the intermediate component holder is further configured to hold a second articulating bearing and to retain the first and second articulating bearings for simultaneous insertion into the space between the end plates.

10. The intervertebral implant delivery system of claim 1, further comprising a compressor configured to be actuated to urge the end plates together to cause the end plates to snap into engagement with one or more intermediate components positioned between the end plates.

11. An intervertebral implant delivery system comprising:
a first end plate holder configured to deliver a first end plate to an intervertebral space from any approach selected from the group consisting of an anterior approach and a lateral approach; and
an intermediate component holder configured to deliver a first intermediate component securable to the first end plate to the intervertebral space from any approach selected from the group consisting of an anterior approach and a lateral approach,
wherein the intermediate component holder comprises an attachment feature rotatable to directly contact and lock with the intermediate component, and rotatable to release the intermediate component.

12. The intervertebral implant delivery system of claim 11, further comprising a pivot assembly couplable to the first end plate holder, wherein at least one of the first end plate holder and the pivot assembly further comprises a support feature attachable to a stationary frame to keep the pivot assembly substantially stationary.

13. The intervertebral implant delivery system of claim 11, further comprising:
a second end plate holder configured to deliver a second end plate to the intervertebral space; and
a first spacer insertable between the first and second end plate holders to urge the end plates toward first and second vertebral bodies, respectively, wherein the first and second vertebral bodies bound the intervertebral space.

14. The intervertebral implant delivery system of claim 11, wherein the first intermediate component comprises a first articulating bearing, wherein the intermediate component holder is further configured to hold a second articulating bearing and to retain the first and second articulating bearings for simultaneous insertion into the intervertebral space.

15. The intervertebral implant delivery system of claim 11, wherein the first end plate holder comprises a first end comprising an expandable retention interface configured to engage any of a plurality of slots on a periphery of the first end plate to couple the first end plate to the first end.

16. An intervertebral implant delivery system comprising:
a first end plate holder configured to deliver a first end plate to an intervertebral space;
a second end plate holder configured to deliver a second end plate to the intervertebral space;
a first articulating bearing comprising a dome-shaped bearing surface;
a second articulating bearing comprising a depression shaped to receive and articulate with the dome-shaped bearing surface; and
an intermediate component holder configured to deliver the first and second articulating bearings to the intervertebral space simultaneously, and independently of delivery of the first and second end plates to the intervertebral space.

17. The intervertebral implant delivery system of claim 16, wherein the first end plate holder, second end plate holder, and intermediate component are configured to deliver the first and second articulating bearing surfaces while holding the first and second end plates substantially stationary.

18. The intervertebral implant delivery system of claim 16, further comprising a pivot assembly that couples the first and second end plate holders together, wherein at least one of the first end plate holder, the second end plate holder, and the pivot assembly comprises a support feature attachable to a stationary frame to keep the pivot assembly substantially stationary.

19. The intervertebral implant delivery system of claim 16, further comprising a first spacer insertable between the first and second end plate holders to urge the end plates toward first and second vertebral bodies, respectively, wherein the first and second vertebral bodies bound the intervertebral space.

20. The intervertebral implant delivery system of claim 16, wherein the intermediate component holder is configured to deliver the first and second articulating bearings to the intervertebral space from any approach selected from the group consisting of an anterior approach and a lateral approach.

21. A method for delivering an intervertebral implant, the method comprising:
 retaining a first end plate of an intervertebral implant with a first end of a first end plate holder;
 retaining a second end plate of the intervertebral implant with a first end of a second end plate holder coupled to the first end plate holder by a pivot assembly;
 inserting the first end plate into an intervertebral space;
 inserting the second end plate into the intervertebral space;
 actuating the second ends of the end plate holders to adjust a height of a space between the end plates and an angulation of the first end plate relative to the second end plate.

22. The method of claim 21, wherein the angulation comprises an anterior-posterior angulation, wherein actuating the second ends comprises actuating the second ends from a lateral approach to determine the angulation.

23. The method of claim 21, further comprising attaching at least one of the first end plate holder, the second end plate holder, and the pivot assembly to a stationary frame to keep the pivot assembly substantially stationary.

24. The method of claim 21, further comprising inserting a first spacer between the first and second end plate holders to urge the end plates toward first and second vertebral bodies, respectively, wherein the first and second vertebral bodies bound the intervertebral space.

25. The method of claim 21, further comprising:
 retaining a first intermediate component with an intermediate component holder; and
 inserting the first intermediate component into the space between the end plates.

26. The method of claim 25, wherein inserting the intermediate component into the space between the end plates comprises:
 selecting an approach from the group consisting of a lateral approach and an anterior approach; and
 inserting the first intermediate component into the space along the selected approach.

27. The method of claim 25, further comprising:
 detaching a second intermediate component from the first and second end plates; and
 removing the second intermediate component from the space prior to insertion of the first intermediate component into the space.

* * * * *